US011173318B2

(12) United States Patent
Maharaj

(10) Patent No.: US 11,173,318 B2
(45) Date of Patent: *Nov. 16, 2021

(54) METHOD OF REPAIRING AGE AND DISEASE IMMUNE DYSFUNCTION AND CELLULAR SENESCENCE WITH LYMPHOID STEM CELLS AND THEN RE-APPLYING THOSE FOR THERAPEUTIC USE

(71) Applicant: ADVANCED NEUROREGENERAIVE THERAPIES, LLC, Boynton Beach, FL (US)

(72) Inventor: Dipnarine Maharaj, Boynton Beach, FL (US)

(73) Assignee: Advanced Neuroregenerative Therapies, LLC., Boynton Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/534,720

(22) Filed: Aug. 7, 2019

(65) Prior Publication Data

US 2020/0215348 A1 Jul. 9, 2020

Related U.S. Application Data

(63) Continuation of application No. 14/889,756, filed as application No. PCT/US2014/037496 on May 9, 2014, now abandoned.

(60) Provisional application No. 61/821,319, filed on May 9, 2013, provisional application No. 61/893,444, filed on Oct. 21, 2013.

(51) Int. Cl.
| | | |
|---|---|---|
| A61K 35/16 | (2015.01) | |
| A61N 2/00 | (2006.01) | |
| A61N 2/02 | (2006.01) | |
| A61K 35/28 | (2015.01) | |
| A61K 38/18 | (2006.01) | |
| A61K 35/12 | (2015.01) | |
| A61K 38/19 | (2006.01) | |

(52) U.S. Cl.
CPC ............. *A61N 2/002* (2013.01); *A61K 35/12* (2013.01); *A61K 35/16* (2013.01); *A61K 35/28* (2013.01); *A61K 38/18* (2013.01); *A61K 38/193* (2013.01); *A61N 2/02* (2013.01)

(58) Field of Classification Search
CPC .............................. A61K 38/193; A61K 38/18
See application file for complete search history.

(56) References Cited

U.S. PATENT DOCUMENTS

| | | |
|---|---|---|
| 4,081,431 A | 3/1978 | Stephan et al. |
| 4,710,381 A | 12/1987 | Kunicki et al. |
| 5,626,617 A | 5/1997 | Brewitt |
| 6,175,057 B1 | 1/2001 | Mucke et al. |
| 6,455,757 B1 | 9/2002 | Mucke et al. |
| 7,078,232 B2 | 7/2006 | Konkle et al. |
| 7,598,049 B2 | 10/2009 | Ray et al. |
| 7,807,458 B2 | 10/2010 | Schiller et al. |
| 8,389,226 B2 | 3/2013 | Ray et al. |
| 8,410,138 B2 | 4/2013 | Wyss-Coray et al. |
| 9,161,968 B2 | 10/2015 | Wyss-Coray et al. |
| 9,636,515 B2 | 5/2017 | Maharaj |
| 2005/0267355 A1 | 12/2005 | Parker |
| 2006/0228795 A1 | 10/2006 | Parker |
| 2007/0269887 A1 | 11/2007 | Coelho et al. |
| 2008/0300176 A1 | 12/2008 | Wu et al. |
| 2009/0117034 A1 | 5/2009 | Chen et al. |
| 2011/0002881 A1 | 1/2011 | Levesque et al. |
| 2014/0356893 A1 | 12/2014 | Mishra |
| 2014/0360944 A1 | 12/2014 | Esteron |

FOREIGN PATENT DOCUMENTS

| | | |
|---|---|---|
| EP | 0582932 A1 | 2/1994 |
| EP | 2144923 A2 | 1/2010 |
| WO | 2005/117696 A2 | 12/2005 |
| WO | 2007/146432 A2 | 12/2007 |
| WO | 2008/124406 A2 | 10/2008 |
| WO | 2011/069121 A1 | 6/2011 |
| WO | 2013/093920 A2 | 6/2013 |
| WO | 2013/111130 A1 | 8/2013 |
| WO | 2014/126931 A1 | 8/2014 |

OTHER PUBLICATIONS

Alegre et al., Bone Marrow Transplantation 20:211-217, (1997).*
Winkler et al., Leukemia, 26: 1994-1601,(2012).*
2_Blood Plasma definition, Merriam Webster Jul. 26, 2018 (2 pages).
Barbara Dietel et al: "Suppression of dendritic cell functions contributes to the anti-inflammatory action of granulocyte-colony stimulating factor in experimental stroke", Experimental Neurology, vol. 237, No. 2, Oct. 1, 2012 (Oct. 1, 2012), pp. 379-387.
Blood plasma definition by Medical dictionary load_on Jul. 26, 2018 (3 pages).
Cashen, et al., "Mobilizing stem cells from normal donors: is it possible to Improve upon G-CSF?", Bone Marrow Transplantation, 2007, 577-588, 39, Nature Publishing Group.

(Continued)

*Primary Examiner* — Gyan Chandra
(74) *Attorney, Agent, or Firm* — DLA Piper LLP (US)

(57) ABSTRACT

This invention relates to methods for treatment of diseases of ageing including immunosenescence, immune dysfunction, inflammation and impairment of early lymphoid lineage differentiation. The invention more specifically relates to the use of granulocyte colony stimulating factors to assist in stem cell mobilization, optionally in combination with the application of a method of delivering precise magnetic field patterns which agree with the body's own natural magnetic field patterns, and further in combination with re-infusion of previously collected autologous cells and/or plasma, optionally including allogeneic (healthy donor) cells and blood plasma.

13 Claims, 26 Drawing Sheets

(56) References Cited

OTHER PUBLICATIONS

Castellano, et al., "Blood-Borne Revitalization of the Aged Brain", Oct. 2015, vol. 72 JAMA Neurology.
Chapter 4_Blood Components by University of Michigan (2004).
De La Rubia, "Follow-up of healthy donors receiving granulocyte colony-stimulating factor for peripheral blood progenitor cell mobilization and collection, Results of the Spanish Donor Registry", Haematologica, 2008, 735-740, 95(5).
Emile L. Boulpaep, p. 429 of Chapter 18, Medical Physiology Book, by Walter F. Boron, Emile L. Boulpaep.
European Search Report and Search Opinion Received for EP Application No. 17159426.0, dated Oct. 16, 2017, 10 pages.
Feldman and Sink (2008).
Harn Horng-Jyh et al: Rejuvenation of aged pig facial skin by transplanting allogeneic granulocyte colony-stimulating factor-induced peripheral blood stem cells from a young pig. Cell Transplantation 2013, vol . 22, No. 4, Feb. 26, 2013 (Feb. 26, 2013), pp. 755-765.
Hill G R et al: "Allogeneic Stem Cell Transplantation with Peripheral Blood Stem Cells Mobilized by Pegylated G-CSF" , Biology of Blood and Marrow Transplantation, Kluge Carden Jennings Publishing, Charlottesville, VA, US, vol. 12, No. 6, Jun. 1, 2006 (Jun. 1, 2006), pp. 603-607.
Holig, "G-CSF in Healthy Allogeneic Stem Cell Donors", Transfusion Medicine and Hemotherapy, 02013, 40, Transfus Med Hemother 225-235.
International Preliminary Report on Patentability received for PCT Patent Application No. PCT/US2014/037496, dated Nov. 19, 2015, 12 pages.
International Search Report and Written Opinion received for PCT Patent Application No. PCT/US2014/037496, dated Jan. 30, 2015, 16 pages.
J L. Winters (Hematology (2012) p. 7-12).
Liu Y-X et al: "Influence of different cytokine groupings on the proliferation of hematopoietic stem cells derived from human umbilical cord blood in vitro" , Zhongguo Zuzhi Gongcheng Yu Linchuang Kangfu = Journal of Clinical Rehabilitative Tissue Engineering Rese, Zhongguo Kangfu Yixuehui, CN, vol . 11, No. 3, Jan. 21, 2007 (Jan. 21, 2007), pp. 401-404.
Matthew B Murphy et al: "Adult and umbilical cord blood-derived platelet-rich plasma for mesenchymal stem cell proliferation, chemotaxis, and cryo-preservation", Biomaterials, Elsevier Science Publishers BV., Barking, GB, vol. 33, No. 21, Apr. 1, 2012 (Apr. 1, 2012), pp. 5308-5316.
Mikirova Nina A et al: "Circulating endothelial progenitor cells: a new approach to anti-aging medicine?", Journal of Translational Medicine, Biomed Central, vol . 7, No. 1, Dec. 15, 2009 (Dec. 15, 2009), p. 106.
Nguyen et al (The Role of Plasmapheresis in Critical Illness, Crit. Care Clin. 28: 453-468, 2012).
Office Action received for European Application No. 14730681, dated Apr. 23, 2019, 7 pages.
Office Action received for European Application No. 14730681, dated Nov. 10, 2017, 5 pages.
Office Action received for European Application No. 17159426, dated Nov. 8, 2018, 10 pages.
Pamphilion et al., "The use of granulocyte colony-stimulating factor in volunteer blood and marrow regist donors", Bone Marrow Transplantation, 2006, 699-700, 38, Nature Publishing Group.
Rockwood, et al., "A global clinical measure of fitness and frailty in elderly people", CMAJ, Aug. 30, 2005, 489-495, 173(5), CMA Media Inc.
S Spuck et al: "G-CSF application in patients with severe bacterial pneumonia increases IL-10 expression in neutrophils", Respiratory Medicine, vol. 97, No. 1, Jan. 1, 2003 (Jan. 1, 2003), pp. 51-58.
Scudellari, "Ageing research: Blood to blood", Nature, Jan. 21, 2015, 426-429, 517, Nature Publishing Group.
Simko et al., J. Cell. Biochem. 93: 83-92, 2004.
Switzer et al., "Donating slimulated peripheral blood stem cells vs bone marro: do donors experience the procedures differently?", 2001, 917-923, 27, Nature Publishing Group.
UC Davis Cancer Center, "peripheral blood stem cell donation", www.ucdmc.ucdavis.edu/cancer, Dec. 2006, 1-2.
Villeda, et al., "The aging systemic milieu negatively regulates neurogenesis and cognitive function", Nature, Mar. 1, 2012, 90-94, 477.
Vollmar Brigitte et al: "Age-associated loss of immunomodulatory protection by granulocyte-colony stimulating factor in endotoxic rats.", Shock (Augusta, GA.) Oct. 2002, vol. 18, No. 4, Oct. 2002 (Oct. 2002), pp. 348-354.
Wikipedia—Plasma.
Wikipedia—Plasmapheresis.
Xiao et al., J. Cell. Mol. Med. 11: 1272-1290, 2007.
Xu et al., British J. Haematology, 1996, 93: 558-568.
Zi-Min Sun et al: HLA-matched sibling transplantation with G-CSF mobilized PBSCs and BM decreases GVHD in adult patients with severe aplastic anemia , Journal of Hematology & Oncology, Biomed Central Ltd, London UK, vol. 3, No. 1, Dec. 31, 2010 (Dec. 31, 2010), p. 51.

\* cited by examiner

Natural complex biologic waveforms of a frog nerve

Magnetic field generation by current flow

Patient 2

Patient 2

Patient 3

Patient 4

Patient 4

Patient 5

Patient 5

Patient 5

Patient 6

Patient 7

Patient 7

Patient 8

METHOD OF REPAIRING AGE AND DISEASE IMMUNE DYSFUNCTION AND CELLULAR SENESCENCE WITH LYMPHOID STEM CELLS AND THEN RE-APPLYING THOSE FOR THERAPEUTIC USE

CROSS-REFERENCE TO RELATED APPLICATIONS

This application is a continuation application of U.S. application Ser. No. 14/889,756, filed Nov. 6, 2015; which is a 35 USC § 371 National Stage application of International Application No. PCT/US2014/037496 filed May 9, 2014; which claims the benefit under 35 USC § 119(e) to U.S. Application Ser. No. 61/821,319 filed May 9, 2013; and the benefit under 35 USC § 119(3) to U.S. Application Ser. No. 61/893,444, filed Oct. 21, 2013. The disclosure of each of the prior applications is considered part of and is incorporated by reference in the disclosure of this application.

FIELD OF THE INVENTION

This invention relates to methods for treatment of diseases of ageing including immunosenescence, immune dysfunction, inflammation and impairment of early lymphoid lineage differentiation. The invention more specifically relates to the use of granulocyte colony stimulating factors to assist in stem cell mobilization, optionally in combination with the application of a method of delivering precise magnetic field patterns which agree with the body's own natural magnetic field patterns, and further in combination with re-infusion of stem cell containing compositions, such as previously collected autologous cells and/or plasma, optionally including allogeneic (healthy donor) cells and blood plasma.

BACKGROUND OF THE INVENTION

The phenomenon which manifests as growth arrest after a period of apparently normal cell proliferation is known as Replicative Senescence (RS). Replicative Senescence is seen in a) cells from adults of all ages b) embryonic tissues, and c) animals.

Aging is associated with alterations of the immune system including impairments in innate immunity, T-lymphopoiesis and B-lymphopoiesis and these impairments contribute to immunosenescence and immune dysfunction in affected individuals. Multipotent hematopoietic stem cells (HSCs) aging contributes to impairments in early lymphoid lineage differentiation Immunosenescence with immune dysfunction and increased inflammation is a primary cause of aging and diseases such as anemia, chronic diseases, autoimmune disorders, cancer, cardiovascular diseases, infection, metabolic diseases, neurodegenerative diseases, protein energy malnutrition and frailty.

Oscillating magnetic fields have been used for years in the course of administering physical therapy to clinic patients suffering from bone fractures. These devices are typically called bone growth stimulators. Bone growth occurs as a result of stem cell stimulation, activation and differentiation. These device signals, however, are a series of pulses or oscillating waves, which have symmetry typical of electronic-generated signals (see FIG. 1 "Common electronic-generated signals"). More recently, researchers have discovered that the body emits its own complex electromagnetic field pattern. Unique patterns are associated with immunosenescence and immune dysfunction, stress, or disease. By capturing these abnormal patterns, re-storing and re-admitting these patterns to the target patient, researchers theorize that the normal "healing process" may be restored more effectively, as the patterns would be natural biologic patterns.

What is unique about the instantly disclosed method described is the confluence of these unique processes to promulgate a therapeutic modality.

The number of Cumulative population doublings (CPDs) cells undergo in culture varies considerably between cell types and species. Early results suggested a relation between CPDs cells could endure and the longevity of the species from which the cells were derived, e.g. cells from the Galapagos tortoise, which can live over a century, divide about 110 times while mouse cells divide roughly 15 times. Cells taken from patients with progeroid syndromes such as Werner syndrome (WS)-exhibit far fewer CPDs than normal humans. Certain "immortal" cell lines can divide indefinitely without reaching RS, e.g. embryonic germ cells and most cell lines derived from tumors, such as HeLa cells.

Biomarkers of cell senescence include:
1) Growth arrest—Senescent cells are growth arrested in the transition from phase G1 to phase S of the cell cycle. The growth arrest in RS is irreversible in the sense that growth factors cannot stimulate the cells to divide even though senescent cells can remain metabolically active for long periods of time;
2) Cellular morphology—Senescent cells are bigger and a senescent population has more diverse morphotypes than cells at earlier CPDs (Note FIG. 12 which shows Normal human fibroblasts (left) and fibroblasts showing a senescent morphology (three cells on the right). Notice the common elongated morphology of senescent cells.
3) Senescence-associated β-galactosidase (SA β-gal) activity—In vitro and in vivo, the percentage of cells positive for SA β-gal increases with, respectively, CPDs and age. In immortal cell lines, such as HeLa tumor cells, the percentage of cells positive for SA β-gal does not correlate with CPDs. The increase in SA β-gal also correlates with the appearance of the senescent morphotypes;
4) Polyploid Increase—the percentage of polyploid cells—i.e., cells with three or more copies of chromosomes—has been shown to increase. Deletions in the mitochondrial DNA (mtDNA) have also been observed both during RS and during aging in vivo, at least in some cells;
5) Change in Gene Expression Levels—The expression levels of several genes change during in vitro cellular aging One important type of gene overexpressed in senescent cells are inflammatory regulators like interleukin 6 (IL6); proinflammatory proteins secreted by senescent cells in driving senescence, which may lead to positive feedback loops and to senescence induction in normal cells near senescent cells;
6) Metalloproteinase and Heat Shock Protein Production—Senescent cells also display an increased activity of metalloproteinases which degrade the extracellular matrix and a decreased ability to express heat shock proteins;
7) Telomere shortening—the primary cause of RS in human fibroblasts which have a major role in aging.

SUMMARY OF THE INVENTION

The phenomenon which manifests as growth arrest after a period of apparently normal cell proliferation is known as Replicative Senescence (RS). Replicative Senescence is seen in a) cells from adults of all ages b) embryonic tissues, and c) animals. The instant invention discloses treatment modalities for treating a number of maladies which result from the aging process.

Aging is associated with alterations of the immune system including impairments in innate immunity, T-lymphopoiesis and B-lymphopoiesis and these impairments contribute to immunosenescence and immune dysfunction in affected individuals. Multipotent hematopoietic stem cells (HSCs) aging contributes to impairments in early lymphoid lineage differentiation Immunosenescence with immune dysfunction and increased inflammation is a primary cause of aging and diseases such as anemia, chronic diseases, autoimmune disorders, cancer, cardiovascular diseases, infection, metabolic diseases, neurodegenerative diseases, protein energy malnutrition and frailty.

Oscillating magnetic fields have been used for years in the course of administering physical therapy to clinic patients suffering from bone fractures. These devices are typically called bone growth stimulators. Bone growth occurs as a result of stem cell stimulation, activation and differentiation. These device signals, however, are a series of pulses or oscillating waves, which have symmetry typical of electronic-generated signals (see FIG. 1 "Common electronic-generated signals"). More recently, researchers have discovered that the body emits its own complex electromagnetic field pattern. Unique patterns are associated with immunosenescence and immune dysfunction, stress, or disease. By capturing these abnormal patterns, re-storing and re-admitting these patterns to the target patient, researchers theorize that the normal "healing process" may be restored more effectively, as the patterns would be natural biologic patterns. U.S. Pat. No. 7,361,136 to Parker describes a method of treatment utilizing such a device, and is incorporated by reference herein in its entirety.

The instantly disclosed method describes a therapeutic modality that represents a confluence of one or more of these treatments.

Accordingly, it is a primary objective of the instant invention to treat diseases of ageing, diseases of ageing with immunosenescence and immune dysfunction and inflammation, and impairments in early lymphoid lineage differentiation by use of a stem cell mobilization agents, G-CSF, Granulocyte Colony Stimulating Factor) in combination with one or more of:

collecting autologous stem cells and plasma using a cell collection device;

re-infusing the previously collected autologous cells and or blood plasma;

re-infusing the previously collected autologous cells together with allogeneic (healthy donor) cells and or blood plasma; and re-infusing allogeneic (healthy donor) cells and or blood plasma.

Treating diseases of ageing and diseases of ageing with immunosenescence and immune dysfunction and inflammation by stem cell activation using a method of delivering precise magnetic field patterns which agree with the body's own natural magnetic field patterns, and do so with an instrument capable of routine clinical therapy use, in combination with stem cell mobilization agents, G-CSF, Granulocyte Colony Stimulating Factor) in combination with one or more of:

collecting autologous cells and or plasma using a collection device and re-infusing the previously collected autologous cells and or blood plasma; and re-infusing the previously collected autologous cells and or blood plasma together with allogeneic (healthy donor) cells and blood plasma.

Treating diseases of ageing and diseases of ageing with immunosenescence and immune dysfunction and inflammation by stem cell activation using a method of delivering precise magnetic field patterns which agree with the body's own natural magnetic field patterns, utilizing an instrument capable of routine clinical therapy use, in combination with healthy donor allogeneic cells and/or blood plasma.

Treating diseases of ageing and diseases of ageing with immunosenescence and immune dysfunction and inflammation by stem cell activation using a method of delivering precise magnetic field patterns which agree with the body's own natural magnetic field patterns, utilizing an instrument capable of routine clinical therapy use, in combination with stem cell mobilization agents, G-CSF, Granulocyte Colony Stimulating Factor)

Treating diseases of ageing and diseases of ageing with immunosenescence and immune dysfunction and inflammation by stem cell activation using a method of delivering precise magnetic field patterns which agree with the body's own natural magnetic field patterns, utilizing an instrument capable of routine clinical therapy use.

Treating diseases of ageing and diseases of ageing with immunosenescence and immune dysfunction and inflammation by stem cell activation using a method of delivering precise magnetic field patterns which agree with the body's own natural magnetic field patterns, utilizing an instrument capable of routine clinical therapy use, in combination with autologous cells and/or blood plasma.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
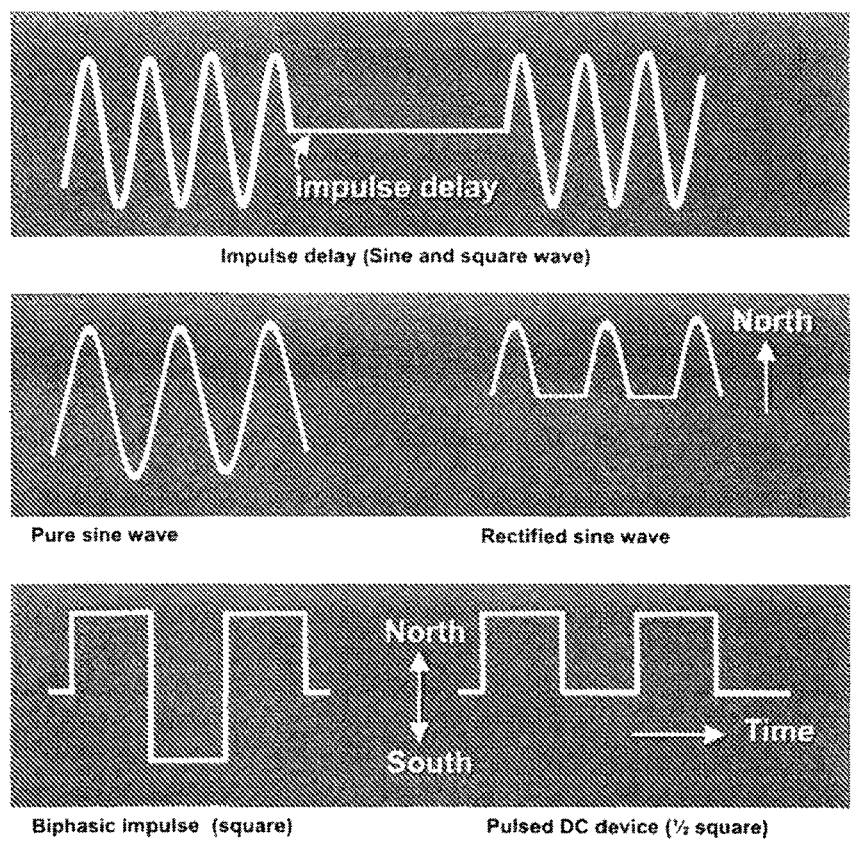
FIG. 1 illustrates common electronic-generated signals.
Figure 2:
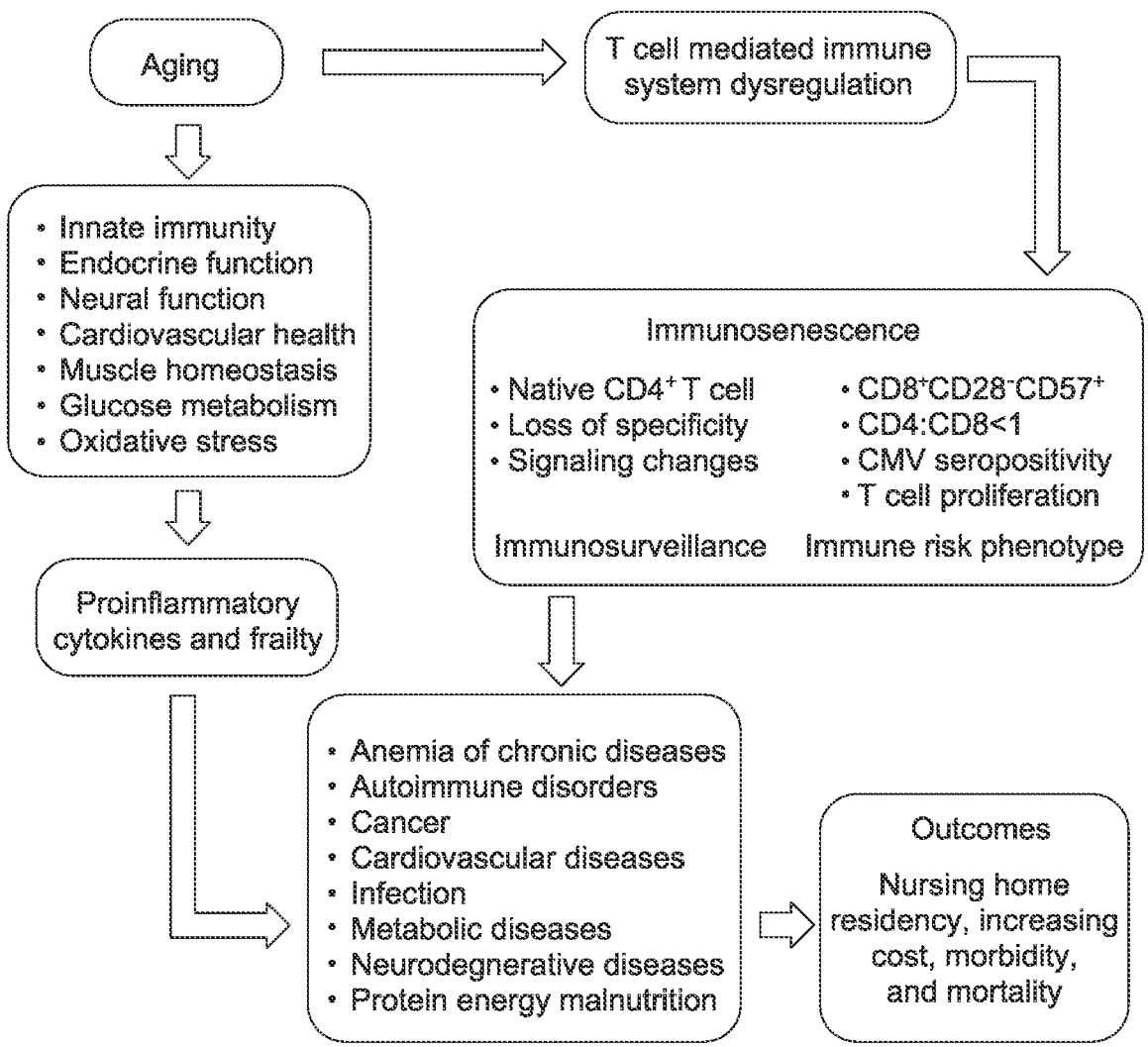
FIG. 2 illustrates the relationship between aging, immunosenescence, inflammation and disease states.

Aging is associated with alterations of the immune system including impairments in innate immunity, T-lymphopoiesis and B-lymphopoiesis and these impairments contribute to immunosenescence in affected individuals.

An altered differentiation capacity of Hematopoietic stem cells (HSCs) has been causally linked to a reduction in lymphopoiesis during aging in mice and in man. Whole genome expression analyses indicated that HSC intrinsic alterations in gene expression contribute to this phenotype. The pool of HSCs comprises different HSC subpopulations that are biased toward myeloid or lymphoid differentiation. There is evidence that upon aging myeloid-biased HSCs are maintained, whereas lymphoid-biased HSCs get lost. These result in the imbalance in myelolymphopoiesis occurring with aging. The molecular causes of this age-associated selection of HSC subpopulations remain to be delineated.

Accumulation of DNA damage has been associated with aging of IISCs in both mice and man. Moreover, studies on telomerase knockout mice (Terc −/−) revealed evidence that chronic DNA damage signaling in response to telomere dysfunction leads to an acceleration of hematopoietic skewing with a strong decrease in lymphopoiesis involving both cell intrinsic checkpoints and alterations in the blood circulatory environment. HSC aging contributes to impairments in early lymphoid lineage differentiation. This process associates with a selective increase of myeloid-competent HSCs and a decrease in lymphoid-competent IISCs during aging. This age-associated skewing in the maintenance of subpopulations of HSCs contributes to defects in lymphopoiesis and decreasing immune function during aging. Molecular mechanisms that can induce stem cell aging include the accumulation of DNA damage and telomere dysfunction and it is possible that stem cell intrinsic checkpoint as well as alteration in the stem cell environment (niche and systemic environment) can contribute to age-dependent selection of HSC subpopulations. The selective survival of distinct subpopulations of HSCs also contributes to the development of malignancies in the hematopoietic system and the selective maintenance of myeloid-competent HSCs enhances the risk of mutation accumulation in the myeloid lineage thereby leading to an increase of myelo-proliferative diseases during aging. The loss of lymphoid-competent HSCs may induce lymphoid lineage derived malignancies by impairing proliferative competition in lymphoid progenitor cell niches. Along these lines it has been shown that age-associated impairments in hematopoietic progenitor cell proliferation select for an outgrowth of malignant clones. In contrast to the possible influences on tumor promotion, it is conceivable that the depletion of HSC subpopulations could serve as a tumor suppressor mechanism involved in the depletion of damaged HSCs. Cell surface marker combinations can subdivide human hematopoietic cells into different subpopulations which can also be subdivided into lymphoid-competent and/or myeloid-competent subpopulations during human aging. The stepwise process of the lymphoid differentiation of multipotent hematopoietic stem cells (HSCs) in human bone marrow has been assumed to begin with expression of the cell surface antigen CD10 (CALLA or MME) on CD34+ progenitors, based on the finding that CD10+ progenitors lack myeloid and erythroid potential but are able to generate all lymphoid lineages. However, subsequent studies have shown that CD34+, CD10+ cells, even those without expression of lineage markers (Lin−: CD3−, CD14−, CD15−, CD19−, CD56−, CD235a−), show a strong bias toward B cell potential with relatively little T cell or natural killer (NK) cell potential. CD34+, Lin−, CD10+ cells that lack expression of CD24 are precursors of the CD34+, Lin− CD10+CD24+ population but nonetheless show molecular evidence of commitment to the B cell lineage, with expression of several B cell-specific genes. L-selectin (CD62L) is expressed on lymphocytes and mediates homing to peripheral lymphoid organs. Studies have reported that upregulation of CD62L expression on c-Kit+Lin−Sca-1+ mouse bone marrow cells correlates with loss of erythroid and megakaryocyte potential and efficient thymic engraftment. In the progenitor hierarchy of the lymphoid commitment of human cells, a stage of lymphoid priming that precedes commitment to the B lymphoid lineage, either before or independently of CD10 expression is a CD34+, Lin−, CD10− progenitor subpopulation in human bone marrow that has high expression of CD62L and that is devoid of clonogenic myeloid or erythroid potential. In stromal cultures, these cells are able to generate B cells, NK cells and T cells, as well as monocytic and dendritic cells.

Aging is associated with alterations of the immune system including impairments in T-lymphopoiesis and B-lymphopoiesis and these impairments contribute to immunosenescence in affected individuals Immunosenescence with immune dysfunction and increased inflammation is a primary cause of aging and diseases such as anemia of chronic diseases, autoimmune disorders, cancer, cardiovascular diseases, infection, metabolic diseases, neurodegenerative diseases, and protein energy malnutrition.

Figure 3:
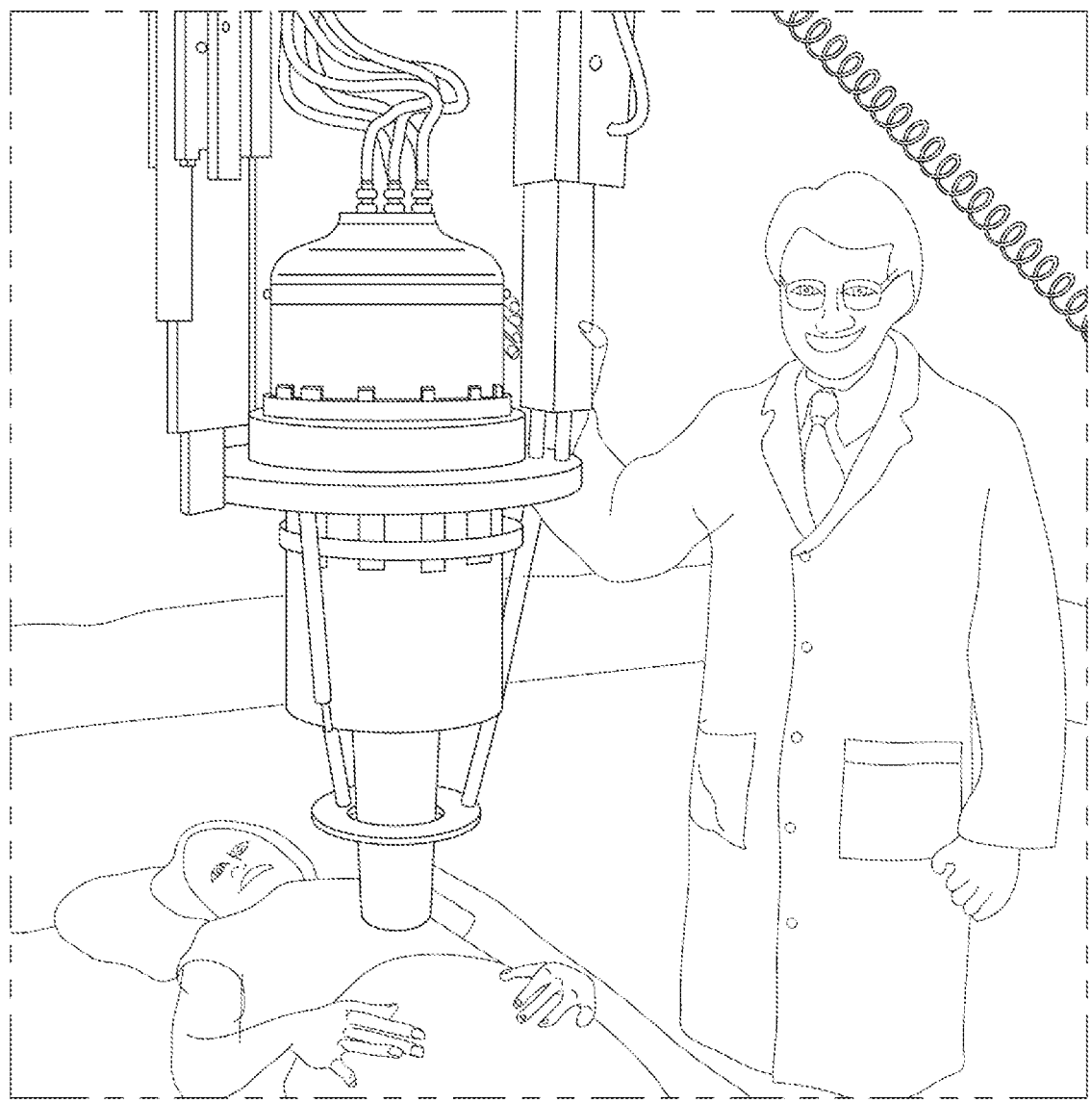
FIG. 3 illustrates a SQUID installation at Vanderbilt University.
Figure 4:
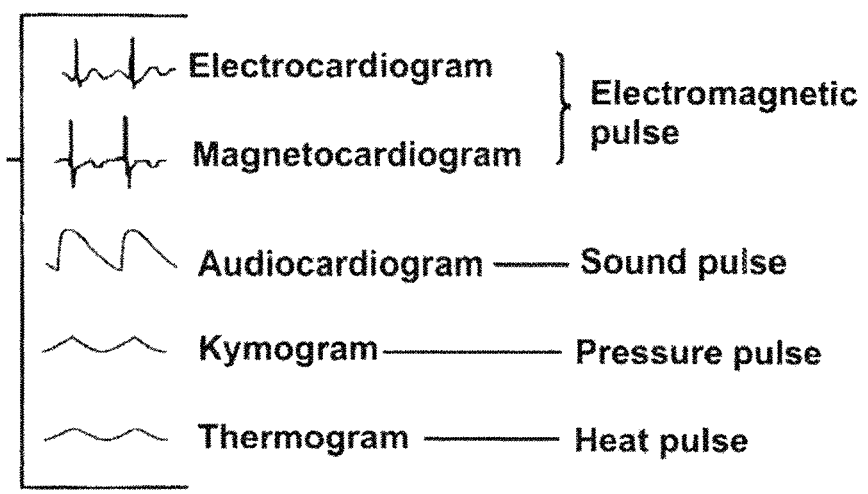
FIG. 4 illustrates natural complex biologic waveforms found in the body.

Natural magnetic field waveforms have been discovered associated with biologic processes ever since the discovery and development of the SQUID (FIG. 3 "SQUID installation at Vanderbilt University"). These waveforms appear in complex patterns such as shown here in (FIG. 4 "Natural complex biologic waveforms found in the body").

Figure 6:
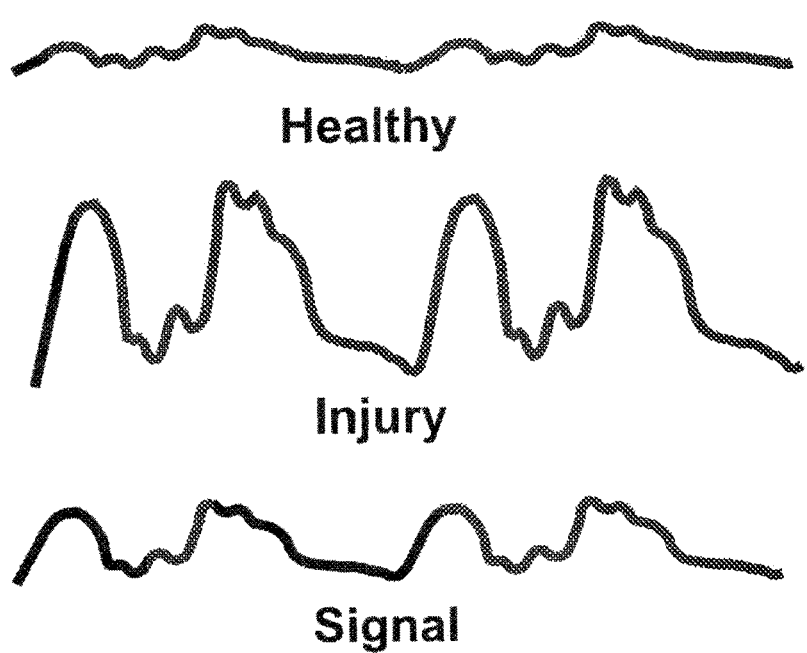
FIG. 6 illustrates the concept of extracting, analyzing and deriving waveforms.

Although there is nothing new about the measurement and recording of these waveform the application of these waveforms in a useful clinic device has just recently been possible through the advance of modern electronics. Thus the method of identification, extraction and isolating and then delivering those magnetic field patterns in a therapeutically effective manner is a primary objective of the invention (FIG. 6 "Extract, analyze and derive").

Researchers have theorized since the late 1960's that the information content of a magnetic field waveform is received and recognized by the body (if delivered in a specific manner) and is useful for therapeutic effects. The modern bone growth stimulator is one example of such a device, whereby this device has proven useful in medical applications to enhance the repair and growth of bone tissue. The method and device to deliver according to the method should, in theory, prove to be more effective in delivering medical therapy to a patient.

Natural biologic waveforms have been measured for many body processes. The graphic (FIG. 4 "Natural complex biologic waveforms found in the body") describes several of these processes. More recently, sophisticated and sensitive recording technology has been used to record biologic processes with even greater sensitivity, such as the firing of a single nerve axon. Biologic waveforms have also been associated with specific diseases and inflammatory processes which cause activation of stem cells local to the disease site and being mobilized from the bone marrow into the blood to reach the disease site. These waveforms are speculated to have an association with the body's natural healing processes. Researchers have also speculated that external electromagnetic signals applied to the body are ignored unless they are:

Damaging signals, such as ionizing signals (e.g. X-Ray)
    Benign signals which affect a site of injury (e.g. diseases of ageing and diseases of ageing with immunosenescence and immune dysfunction and inflammation).

The device proposed herein is to deliver natural biologic waveform electromagnetic fields to a site of injury, and so function more effectively than the signals used previously in combination with methods of enhancing the concentration of stem cells at the disease sites. The method is the actual use of these natural biologic waveforms in the generation and delivery of those waveforms suited to a particular injury.

Process to Capture, Store and Replicate Biologic Waveforms

The entire process begins with:
    Discovery of the biologic signal
    Isolation of the repair signal
    Storage of the repair signal
    Generation of the repair signal
    Delivery of the repair signal
    Conformity to a specified protocol Discovery of the Biologic Signal The discovery process begins with a known pathologic condition. For example, a cancer has well-understood biologic processes at work which serve to repair the immune dysfunction and immune senescence and inflammation. These processes all involve the generation and emitting of natural biologic waveforms.

Figure 5:
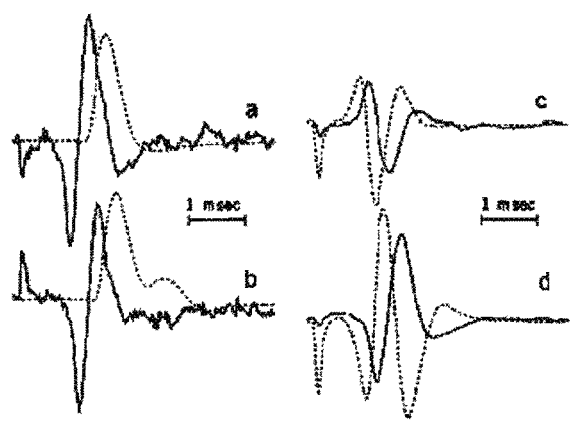
FIG. 5 illustrates natural complex biologic waveforms of a frog nerve.

The discovery, therefore, begins with a patient who has a known condition and a sensitive measurement device, known as a SQUID (Superconductive QUantum Interference Device), to detect and measure the condition waveforms. This device, or a representative of the device, is shown in FIG. 3 "SQUID installation at Vanderbilt University". The waveforms generated by the body or biologic organisms have certain specific characteristics. Examples of certain waveforms are shown in FIG. 5 "Natural complex biologic waveforms of a frog nerve".

The measurement of the natural biologic waveform caused by the underlying pathologic condition is facilitated by the SQUID apparatus, which is routinely used for measuring those types of waveforms. Conversely, the body may emit certain natural biologic waveforms that are associated with the normal biologic function. That is, those waveforms are captured from a healthy subject.

Isolation of the Repair Signal

The natural biologic waveform of the patient target pathology and the patient injury-free target are expected to differ in certain characteristics. In fact, Romanian researchers have reported in the literature that these signals do indeed exist and can be isolated. The isolation process may take place by digitizing those waveforms, analyzing and then performing certain digital operations on the patterns, using pattern-recognition or other graphical technology. Isolation of the waveforms is a straightforward procedure, by which measurements are taken of:

A healthy subject
    A subject with diseases of ageing and diseases of ageing with immunosenescence and immune dysfunction and inflammation Each measurement is captured and digitized using mechanical or electrical conversion means and placed into a common file format. The procedure to further isolate the suspected natural biologic signal is a process whereby a comparison of the two waveforms yields a "difference" waveform (see "Extract, analyze and derive" on page 10), which is then presented as the suspected biologic waveform contributing to the healing process.

The original source waveforms, e.g. the "Disease" waveform, and The "Normal" waveform are used as reference waveforms, in a study to compare the relative effectiveness of those waveforms against the "difference" waveform.

Store of the Repair Signal

The final selected repair signal is then stored in electronic form, typically in a digitized fashion, or it may be stored in printed graphical form. This may use a common flat-file or relational database for the electronic storage medium.

Generation of the Repair Signal

The stored electrical signal pattern is then re-generated in a device (here called a Modulator) which then powers an external applicator. The re-generation of these electrical patterns may take place in a number of ways:

Using an internal digital look-up table
    Using an internal derived equation, which is then solved
    Using a series of signals, such as is found in a fourier series Once the basic repair signal is then re-generated, it is then modulated as to:
    Frequency
    Intensity
    Duty Cycle by the generating device. This final signal is then amplified and prepared for delivery to the patient or subject.

Delivery of the Repair Signal

Figure 7:
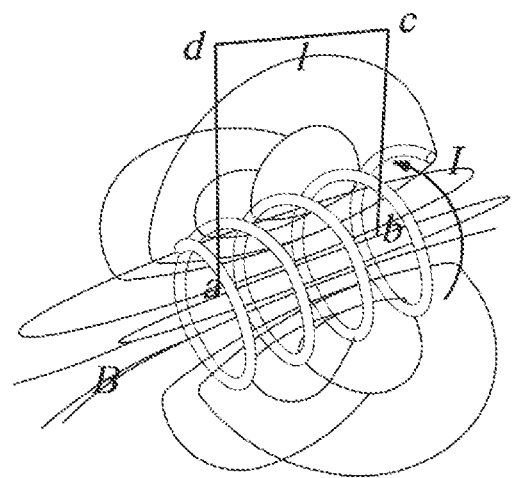
FIG. 7 illustrates magnetic field generation by current flow.

The repair signal, having been captured, stored, processed and modulated, is now ready to be delivered. Magnetic fields are delivered by passing a current through a wire loop assembly of various forms, as is generically illustrated in FIG. 7. These types may be:

A solenoid
A toroid
A planar (or flat) coil
A Helmholtz coil

Figure 8:
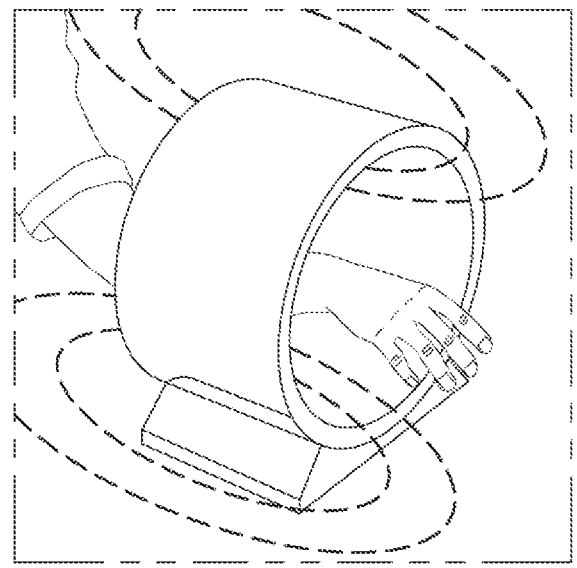
FIG. 8 illustrates use of a solenoid design field generator.
Figure 9:
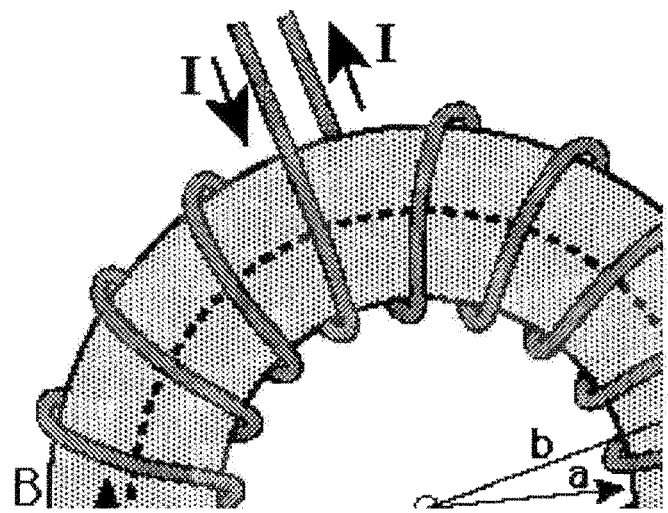
FIG. 9 illustrates a toroidal magnetic field applicator.
Figure 10:
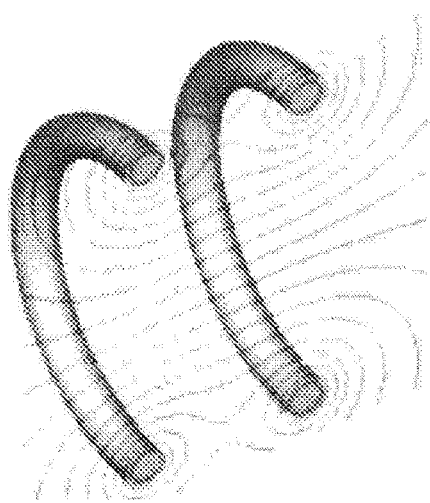
FIG. 10 illustrates a Helmholtz coil field applicator.
Figure 11:
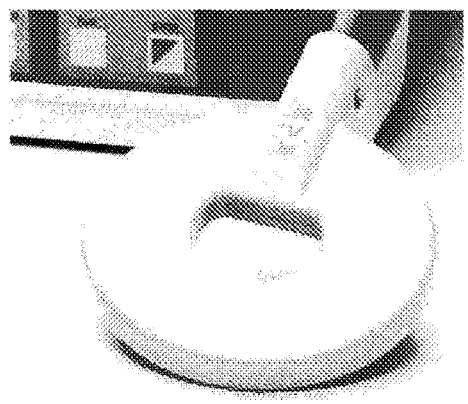
FIG. 11 illustrates a planar field applicator.
Figure 12:
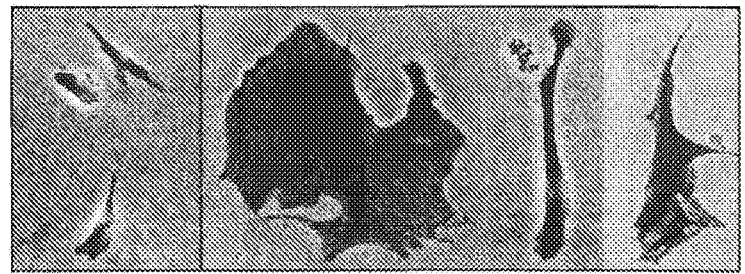
FIG. 12 illustration of normal versus senescent cell morphology.

The solenoid magnetic field pattern may be seen in FIG. 8 "Use of solenoid design". The toroid magnetic field patterns may be seen in FIG. 9 "Toroidal magnetic field applicator". The planar coil design may be seen on FIG. 11 "Planar field applicator". The Helmholtz design may be seen on FIG. 10 "Helmholtz coil field applicator".

Prior to delivering the current to the various types of applicators, the Modulator power must amplify the stored signals to the level whereby they may energize the coils. This amplification may require the expenditure of power levels of up to 500 watts in the case of linear amplification, or may be significantly lower in the case of a switching-type (digital) design.

Conformity to a Specified Protocol

The conformity to a specified protocol may require specifying certain types of stage treatment procedures. These procedures typically require:

A certain time of administered exposure
A certain time between exposures
A certain exposure dose
A certain dose design
A certain dose duty cycle For example, the administered exposure may require stages exposures of 30, 60 or 90 minute exposures over the course of several days. The exposures may be staged according to a certain delay between each exposure. The dosage may be adjusted up or down according to the needs of the subject. The dose design itself is specified, according to a selection of one or several types of waveforms which are stored in the machine, and the dose may have to regulated according to a certain duty cycle.

Various embodiments of the invention are illustrated in the following examples.

Example 1

This protocol will assess the efficacy of stem cell activation with stem cell mobilization using a granulocyte colony stimulating factor (g-csf) and autologous stem cell rich plasma to improve the levels of anti-aging bio-markers in the recipients They will receive daily G-CSF at a dose of 5 to 15 ug/kg intravenously or subcutaneously for 5-7 days monthly for 12 months. Assessments measuring the anti-aging bio-markers and clinical markers of aging as reported via a 13-item Clinical evaluation will be done at baseline before starting treatments and will be repeated every 3 months during the treatment period, and every three months for 12 additional months after the completion of the treatment period. Half of the recipients will be randomly selected to also receive Autologous Stem Cell Rich plasma in aliquots of 50 ml monthly for 12 months in the second 12 month study period. The Autologous plasma donors are also plasma recipients. Autologous Donors will be dosed with G-CSF for three days prior to undergoing plasmapheresis. This will stimulate a significantly increased number of stem cells in the plasma.

The yield of stem cell rich plasma expected from the pheresis is about 2 liters. The plasma will be divided into aliquots of about thirty-six 50 ml doses and 5 ml testing aliquots. Samples will be frozen until such time as the same Plasma Recipient is being treated.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Safety Assessments:

Baseline physical exam, blood chemistry will be done on all recipients at baseline. These will be repeated after 3, 6, 9, and 12 months of treatment, and quarterly for 1 year following the completion of the last treatment.

Safety and tolerability will be monitored through continuous reporting of adverse events.

Example 2

This protocol will assess the efficacy of stem cell activation with stem cell mobilization with granulocyte colony stimulating factor G-CSF) and autologous stem cell rich plasma to improve the levels of anti-aging bio-markers in the recipients.

Patients will be treated with G-CSF stem cell mobilization and Autologous Stem Cell Rich Plasma to improve the levels of anti-aging biomarkers in the recipients.

Primary Objective:

During treatment, patients will continue to be evaluated for improvement in the levels of anti-aging biomarkers in the recipients during treatment for one year and for one year following the end of treatment.

Secondary Objectives:

Improvement of clinical markers of aging as reported via a 13-item Clinical evaluation Study Design:

The study is classified as Phase I/II since it will be using a long-standing safe 'drug' (G-CSF; Autologous plasma; ergo Phase II) but in a novel way (ergo Phase I).

They will receive daily G-CSF at a dose of 5 to 15 ug/kg intravenously or subcutaneously for 5-7 days monthly for 12 months. On the first of the 5-7 day period they will also receive Autologous Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for 5-7 days for three days prior to undergoing plasma pheresis. This will stimulate a significantly increased number of stem cells in the plasma. The yield of stem cell rich plasma expected from the pheresis is about 2 liters. The plasma will be divided into aliquots of about thirty-six 50 ml doses and 5 ml testing aliquots. Samples will be frozen until such time the same Plasma Recipient is being treated.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1) Immunosenescence Panel
2) CCL 11
3) TGFBeta 1 growth factor
4) Nuclear Factor kappa beta (NFkB)
5) DHEA-S
6) Plasma Insulin
7) Telomere length
8) Cytokine Multiplex 18

There will also be clinical markers (group of 13) evaluated at the quarterly visits during physical exam that will provide secondary efficacy data for evaluation.

Example 3

This protocol will assess the efficacy of stem cell activation with stem cell mobilization with granulocyte colony stimulating factor (G-CSF) and autologous stem cell rich plasma in combination with infusing stem-cell rich plasma from ABO-matched cord blood healthy allogeneic donors to improve the levels of anti-aging bio-markers in the recipients.

Patients will be treated with G-CSF stem cell mobilization and Autologous Stem Cell Rich Plasma in combination with Infusing Stem-Cell Rich Plasma from ABO-matched Healthy Cord Blood Allogeneic donors to improve the levels of anti-aging biomarkers in the recipients.

Adults who are interested in assessing their level of anti-aging biomarkers, and who are willing to receive doses of G-CSF stem cell mobilization as well as Autologous Stem Cell Rich Plasma and Infusions of Stem-Cell Rich Plasma from ABO-matched Healthy Cord Blood Allogeneic Donors will be treated monthly for a one-year period to determine if there is any improvement in those markers.

They will receive daily G-CSF at a dose of 5 to 15 ug/kg intravenously or subcutaneously for 5-7 days monthly for 12 months. On the first of the 5-7 day period they will also receive Autologous Stem Cell Rich plasma in aliquots of 50 ml monthly for 12 months. After the end of the daily G-CSF for the 5-7 day period they will also receive Allogeneic Cord Blood Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for three days prior to undergoing plasmapheresis. This will stimulate a significantly increased number of stem cells in the plasma.

The yield of stem cell rich plasma expected from the pheresis is about 2 liters. The plasma will be divided into aliquots of about thirty-six 50 ml doses and 5 ml testing aliquots. Samples will be frozen until such time as the same Plasma Recipient is being treated.

Allogeneic Cord Blood Plasma Donors:

All donations of cord blood plasma will be taken from the plasma extracted and normally discarded from healthy babies cord blood collected from the delivered placenta at the time of birth and whose stem cells are to be cryopreserved for the baby's personal use at a later date.

The yield of plasma expected from the cord blood is about 55 mls. The plasma will be divided into aliquots of 50 ml doses and 5 ml testing aliquots (for cross matching). Samples will be frozen until such time as a Plasma Recipient of the same AB 0/Rh type is being treated.

Based on the average prevalence of ABO types, it is anticipated that the number of donors needed will be approximately 12 to 15 per recipient.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 4

Recipients will be treated with G-CSF stem cell mobilization and Autologous Stem Cell Rich Plasma in combination with Infusing Stem-Cell Rich Plasma from ABO-matched Healthy Allogeneic Donors to improve the levels of anti-aging biomarkers in the recipients.

Recipients who are interested in assessing their level of anti-aging biomarkers, and who are willing to receive doses of G-CSF stem cell mobilization as well as Autologous Stem Cell Rich Plasma and Infusions of Stem-Cell Rich Plasma from ABO-matched Healthy Allogeneic Donors will be treated monthly for a one-year period to determine if there is any improvement in those markers. I).

They will receive daily G-CSF at a dose of 5 to 15 ug/kg intravenously or subcutaneously for 5-7 days monthly for 12 months. On the first of the 5-7 day period they will also receive Autologous Stem Cell Rich plasma in aliquots of 50 ml monthly for 12 months. After the end of the daily G-CSF for the 5-7 day period they will also receive Allogeneic Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for three days prior to undergoing plasma pheresis. This will stimulate a significantly increased number of stem cells in the plasma. The yield of stem cell rich plasma expected from the pheresis is about 2 liters. The plasma will be divided into aliquots of about thirty-six 50 ml doses and 5 ml testing aliquots. Samples will be frozen until such time the same Plasma Recipient is being treated.

Allogeneic Stem Cell Rich Plasma Donors:

The other group making up the study population will be Allogeneic plasma donors. Donors will be dosed with G-CSF at a dose of 5 to 15 ug/kg intravenously or subcutaneously for three days prior to undergoing plasma pheresis. This will stimulate a significantly increased number of stem cells in the plasma. Donors will have Infectious Disease testing repeated on the day of pheresis.

The yield of plasma expected from the pheresis is about 2 liters. The plasma will be divided into aliquots of about thirty-six 50 ml doses and 5 ml testing aliquots (for cross matching). Samples will be frozen until such time as a Plasma Recipient of the same ABO/Rh type is being treated. Donors will be restricted to males and nulliparous females to avoid the presence of cytotoxic lymphocyte and granulocyte antibodies.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 5

This protocol will assess the efficacy of stem cell activation with stem cell mobilization with granulocyte colony stimulating factor (G-CSF) and in combination with infusing stem-cell rich plasma from AB 0-matched healthy allogeneic donors to improve the levels of anti-aging bio-markers in the recipients.

Patients will be treated with G-CSF stem cell mobilization and in combination with Infusing Stem-Cell Rich Plasma from ABO-matched Healthy Allogeneic Donors will be monitored for the improvement of levels of anti-aging biomarkers in the recipients.

Recipients who are interested in assessing their level of anti-aging biomarkers, and who are willing to receive doses of G-CSF stem cell mobilization and Infusions of Stem-Cell Rich Plasma from ABO-matched Healthy Allogeneic Donors will be treated monthly for a one-year period to determine if there is any improvement in those markers. Recipients will receive daily G-CSF at a dose of 5 to 15 ug/kg intravenously or subcutaneously for 5-7 days monthly for 12 months. After the end of the daily G-CSF for the 5-7 day period they will also receive Allogeneic Stein Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Allogeneic Stem Cell Rich Plasma Donors:

Donors will be dosed with G-CSF at a dose of 5 to 15 ug/kg intravenously or subcutaneously for three days prior to undergoing plasma pheresis. This will stimulate a significantly increased number of stem cells in the plasma. The yield of plasma expected from the pheresis is about 2 liters. The plasma will be divided into aliquots of about thirty-six 50 ml doses and 5 ml testing aliquots (for cross matching). Samples will be frozen until such time as a Plasma Recipient of the same ABO/Rh type is being treated. Donors will be restricted to males and nulliparous females to avoid the presence of cytotoxic lymphocyte and granulocyte antibodies.

There will be eight primary biomarker measurements evaluated at baseline, and after treatment for 3 months, 6 months, 9 months, and 12 months. These same evaluations will continue every three months for an additional year to examine the long-term effect of the treatment. These assessments arc:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 6

This protocol will assess the efficacy of stem cell activation with stem cell mobilization with granulocyte colony stimulating factor (G-CSF) and autologous stem cell rich plasma in combination with infusing stem-cell rich plasma from ABO-matched healthy allogeneic donors to improve the levels of anti-aging bio-markers in the recipients.

Patients will be treated with G-CSF stem cell mobilization and Autologous Stem Cell Rich Plasma in combination with Infusing Stem-Cell Rich Plasma from ABO-matched Healthy Allogeneic Donors in the hope of improving the levels of anti-aging biomarkers in the recipients.

Recipients who are interested in assessing their level of anti-aging biomarkers, and who are willing to receive doses of G-CSF stem cell mobilization as well as Autologous Stem Cell Rich Plasma and Infusions of Stem-Cell Rich Plasma from ABO-matched Healthy Allogeneic Donors will be treated monthly for a one-year period to determine if there is any improvement in those markers.

Recipients will receive daily G-CSF at a dose of 5 to 15 ug/kg intravenously or subcutaneously for 5-7 days monthly for 12 months. On the first of the 5-7 day period they will also receive Autologous Stem Cell Rich plasma in aliquots of 50 ml monthly for 12 months. After the end of the daily G-CSF for the 5-7 day period they will also receive Allogeneic Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for three days prior to undergoing plasma pheresis. This will stimulate a significantly increased number of stem cells in the plasma. The yield of stem cell rich plasma expected from the pheresis is about 2 liters. The plasma will be divided into aliquots of about thirty-six 50 ml doses and 5 ml testing aliquots. Samples will be frozen until such time as the same Plasma Recipient is being treated.

Allogeneic Stem Cell Rich Plasma Donors:

Donors will be dosed with G-CSF at a dose of 5 to 15 ug/kg intravenously or subcutaneously for three days prior to undergoing plasma pheresis. This will stimulate a significantly increased number of stem cells in the plasma. The yield of plasma expected from the pheresis is about 2 liters. The plasma will be divided into aliquots of about thirty-six 50 ml doses and 5 ml testing aliquots (for cross matching). Samples will be frozen until such time as a Plasma Recipient of the same ABO/Rh type is being treated. Donors will be restricted to males and nulliparous females to avoid the presence of cytotoxic lymphocyte and granulocyte antibodies.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCI, 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 7

This protocol will assess the efficacy of stem cell activation with stem cell mobilization with granulocyte colony stimulating factor (G-C SF) in combination with infusing stem-cell rich plasma from ABO-matched cord blood allogeneic donors to improve the levels of anti-aging bio-markers in the recipients.

Patients will be treated with G-CSF stem cell mobilization in combination with Infusing Stem-Cell Rich Plasma from ABO-matched Cord Blood Allogeneic Donors will improve the levels of anti-aging biomarkers in the recipients.

Recipients who are interested in assessing their level of anti-aging biomarkers, and who are willing to receive doses of G-CSF stem cell mobilization as well as Infusions of Stem-Cell Rich Plasma from ABO-matched Cord Blood Allogeneic Donors will be treated monthly for a one-year period to determine if there is any improvement in those markers.

Recipients will receive daily G-CSF at a dose of 5 to 15 ug/kg intravenously or subcutaneously for 5-7 days monthly. After the end of the daily G-CSF for the 5-7 day period, they will receive Allogeneic Cord Blood Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Cord Blood Plasma Donors:

All donations of cord blood plasma will be taken from the plasma extracted and normally discarded from healthy babies cord blood collected from the delivered placenta at the time of birth and whose stem cells are to be cryopreserved for the baby's personal use at a later date. The yield of plasma expected from the cord blood is about 55 mls. The plasma will be divided into aliquots of about 50 ml doses and 5 ml testing aliquots (for cross matching). Samples will be frozen until such time as a Plasma Recipient of the same ABO/Rh type is being treated.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 8

This protocol will assess the efficacy of stem cell activation using the recipients own natural magnetic field patterns in combination with stem cell mobilization with granulocyte colony stimulating factor (G-CSF) and autologous stem cell rich plasma to improve the levels of anti-aging bio-markers in the recipients.

Patients will be treated with G-CSF stem cell mobilization and Autologous Stem Cell Rich Plasma in Combination with administration of precise natural Magnetic fields to improve the levels of anti-aging biomarkers in the recipients and improvement of clinical markers of aging as reported via a 13-item Clinical evaluation Recipients who are interested in assessing their level of anti-aging biomarkers, and who are willing to receive doses of G-CSF stem cell mobilization as well as Autologous Stem Cell Rich Plasma and administration of their own Precise Natural Magnetic fields will be treated monthly for a one-year period to determine if there is any improvement in those markers.

Recipients will receive daily G-CSF at a dose of 5 to 15 ug/kg intravenously or subcutaneously for 5-7 days monthly for 12 months. On the first of the 5-7 day period they will also receive Autologous Stem Cell Rich plasma in aliquots of 50 ml and precise magnetic field patterns which will agree with their body's own natural magnetic field patterns monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for three days prior to undergoing plasma pheresis. This will stimulate a significantly increased number of stem cells in the plasma. The yield of stem cell rich plasma expected from the pheresis is about 2 liters. The plasma will be divided into aliquots of about thirty-six 50 ml doses and 5 ml testing aliquots. Samples will be frozen until such time as the same Plasma Recipient is being treated.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 9

This protocol will assess the efficacy of stem cell activation using the recipients own natural magnetic field patterns in combination with stem cell mobilization with granulocyte colony stimulating factor (G-CSF) and autologous stem cell rich plasma in combination with infusing stem-cell rich plasma from ABO-matched healthy allogeneic donors to improve the levels of anti-aging bio-markers in the recipients.

Patients will be treated with G-CSF stem cell mobilization and Autologous Stem Cell Rich Plasma in combination with Infusing Stem-Cell Rich Plasma from ABO-matched Healthy Allogeneic Donors in Combination with administration of Precise natural Magnetic fields to improve the levels of anti-aging biomarkers in the recipients.

Recipients who are interested in assessing their level of anti-aging biomarkers, and who are willing to receive doses of G-CSF stem cell mobilization as well as Autologous Stem Cell Rich Plasma and Infusions of Stein-Cell Rich Plasma from ABO-matched Healthy Allogeneic Donors and administration of their own Precise Natural Magnetic fields monthly for a one-year period will be treated to determine if there is any improvement in those markers. The recipients will receive daily G-CSF at a dose of 5 to 15 ug/kg intravenously or subcutaneously for 5-7 days monthly for 12 months. On the first day of the 5-7 day period they will also receive Autologous Stem Cell Rich plasma in aliquots of 50 ml and precise magnetic field patterns which will agree with their body's own natural magnetic field patterns monthly for 12 months. After the end of the daily G-CSF for the 5-7 day period they will also receive Allogeneic Stem Cell Rich plasma in aliquots of 50 ml monthly for 12 months. Assessments measuring the biomarkers will be done at baseline before starting treatments and will be repeated every 3 months during the treatment period, and every three months for 12 additional months after the completion of the treatment period. Additionally, clinical markers will be collected at those same time points.

Autologous Donors will be dosed with G-CSF at a dose of 5 to 15 ug/kg intravenously or subcutaneously for three days prior to undergoing plasmapheresis. This will stimulate a significantly increased number of stem cells in the plasma. The yield of stem cell rich plasma expected from the pheresis is about 2 liters. The plasma will be divided into aliquots of about thirty-six 50 ml doses and 5 ml testing aliquots. Samples will be frozen until such time the same Plasma Recipient is being treated.

Allogeneic Stem Cell Rich Plasma Donors:

Allogeneic plasma donors will be healthy, young adults (age 30 or less) with no major medical diagnoses. A physical exam and standard blood chemistry and CBC will determine their eligibility. An ABO/Rh typing, hemoglobinopathy testing and antibody panel will be done on each donor, as well as Infectious Disease testing. Donors will be dosed with G-CSF at a dose of 5 to 15 ug/kg intravenously or subcutaneously for three days prior to undergoing plasma pheresis. This will stimulate a significantly increased number of stem cells in the plasma. Donors will have Infectious Disease testing repeated on the day of pheresis. The yield of plasma expected from the pheresis is about 2 liters. The plasma will be divided into aliquots of about thirty-six 50 ml doses and 5 ml testing aliquots (for cross matching). Samples will be frozen until such time a Plasma Recipient of the same ABO/Rh type is being treated. Donors will be restricted to males and nulliparous females to avoid the presence of cytotoxic lymphocyte and granulocyte antibodies.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation. Baseline physical exam, blood chemistry will be done on all recipients at baseline. These will be repeated after 3, 6, 9, and 12 months of treatment, and quarterly for 1 year following the completion of treatment.

Example 10

This protocol will assess the efficacy of stem cell activation using natural magnetic field patterns in combination with infusing stem-cell rich plasma from ABO-matched healthy allogeneic donors to improve the levels of anti-aging bio-markers in the recipients.

Recipients will be treated with plasma from healthy allogeneic donors who have had stem cell mobilization in Combination with administration of Precise natural Magnetic fields to improve the levels of anti-aging biomarkers in the recipients of the plasma.

Adults who are interested in assessing their level of anti-aging biomarkers, and who are willing to receive doses of donor plasma and on the same day they will also receive precise magnetic field patterns which will agree with their body's own natural magnetic field patterns will be treated monthly for a one-year period to determine if there is any improvement in those markers. The recipients will receive ABO/Rh cross-matched plasma in aliquots of 50 ml monthly for 12 months. On the same day they will receive administration of Precise natural Magnetic fields. Assessments measuring the biomarkers will be done at baseline and every 3 months during the treatment period, and every three months for 12 additional months after the completion of the treatment period. Additionally, clinical markers (group of 13) will be collected at those same time points.

Plasma Donors:

All donors will be healthy, young adults (age 30 or less) with no major medical diagnoses. A physical exam and standard blood chemistry and CBC will determine their eligibility. An ABO/Rh typing and antibody panel will be done on each donor, as well as Infectious Disease testing. Donors will be dosed with G-CSF at a dose of 5 to 15 ug/kg intravenously or subcutaneously for three days prior to undergoing plasma pheresis. This will stimulate a significantly increased number of stem cells in the plasma. Donors will have Infectious Disease testing repeated on the day of pheresis.

The yield of plasma expected from the pheresis is about 2 liters. The plasma will be divided into aliquots of about thirty-six 50 ml doses and 5 ml testing aliquots (for cross matching). Samples will be frozen until such time as a Plasma Recipient of the same ABO/Rh type is being treated. Donors will be restricted to males and nulliparous females to avoid the presence of cytotoxic lymphocyte and granulocyte antibodies.

Recipients can be of any age or gender as long as they have no significant medical issues that would be contraindicated by the infusion of donor plasma and administration of precise magnetic field patterns which will agree with their body's own natural magnetic field patterns. This will be determined by a physical exam and standard blood chemistry and CBC. Their ABO/Rh type will also be tested.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at baseline and at quarterly visits during physical exam that will provide secondary efficacy data for evaluation. Baseline physical exam, blood chemistry and infectious disease markers will be done on all plasma donors and recipients at baseline. These apart from infectious disease markers will be repeated after 3, 6, 9, and 12 months of treatment, and quarterly for 1 year following the completion of treatment.

Example 11

This protocol will assess the efficacy of stem cell activation using natural magnetic field patterns in combination with infusing stem-cell rich plasma from ABO-matched healthy cord blood allogeneic donors to improve the levels of anti-aging bio-markers in the recipients.

Recipients will be treated with plasma from healthy Cord Blood allogeneic donors in combination with administration of Precise natural Magnetic fields to improve the levels of anti-aging biomarkers in the recipients of the plasma.

Recipients who are interested in assessing their level of anti-aging biomarkers, and who are willing to receive doses of Cord Blood donor plasma and on the same day they will also receive precise magnetic field patterns which will agree with their body's own natural magnetic field patterns will be treated monthly for a one-year period to determine if there is any improvement in those markers.

The recipients will receive ABO/Rh cross-matched Cord Blood plasma in aliquots of 50 ml monthly for 12 months. On the same day they will receive administration of Precise natural Magnetic fields. Assessments measuring the biomarkers will be done at baseline and every 3 months during the treatment period, and every three months for 12 additional months after the completion of the treatment period. Additionally, clinical markers will be collected at those same time points.

All donations of cord blood plasma will be taken from the plasma extracted and normally discarded from healthy babies cord blood collected from the delivered placenta at the time of birth and whose stem cells are to be cryopreserved for the baby's personal use at a later date. The baby and mother will have no major medical diagnoses and the mother will sign an informed consent form and agree to donation of cord blood plasma. A physical exam and standard blood chemistry and CBC will determine their eligibility. An ABO/Rh typing and antibody panel will be done on each donor, as well as Infectious Disease testing.

The yield of plasma expected from the cord blood is about 55 mls. The plasma will be divided into aliquots of 50 ml doses and 5 ml testing aliquots (for cross matching). Samples will be frozen until such time as a Plasma Recipient of the same ABO/Rh type is being treated. Based on the average prevalence of ABO types, it is anticipated that the number of donors needed will be approximately 12 to 15 per recipient.

Recipients can be of any age or gender as long as they have no significant medical issues that would be contraindicated by the infusion of donor plasma and administration of precise magnetic field patterns which will agree with their body's own natural magnetic field patterns. This will be determined by a physical exam and standard blood chemistry and CBC. Their ABO/Rh type will also be tested.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at baseline and at quarterly visits during physical exam that will provide secondary efficacy data for evaluation. Baseline physical exam, blood chemistry and infectious disease markers will be done on all plasma donors and recipients at baseline. These apart from infectious disease markers will be repeated after 3, 6, 9, and 12 months of treatment, and quarterly for 1 year following the completion of treatment.

Example 12

This protocol will assess the efficacy of stem cell activation using the recipients own natural magnetic field patterns in combination with stem cell mobilization with granulocyte colony stimulating factor (G-CSF) to improve the levels of anti-aging bio-markers in the recipients.

Patients will be treated with G-CSF stem cell mobilization in combination with administration of Precise natural Magnetic fields to improve the levels of anti-aging biomarkers in the recipients.

Recipients who are interested in assessing their level of anti-aging biomarkers, and who are willing to receive doses of G-CSF stem cell mobilization and administration of their own Precise natural Magnetic fields ill be treated monthly for a one-year period to determine if there is any improvement in those markers.

The recipients will receive daily G-CSF at a dose of 5 to 15 ug/kg intravenously or subcutaneously for 5-7 days monthly for 12 months. On the same day they will also receive precise magnetic field patterns which will agree with their body's own natural magnetic field patterns. Assessments measuring the biomarkers will be done at baseline before starting treatments and will be repeated every 3 months during the treatment period, and every three months for 12 additional months after the completion of the treatment period. Additionally, clinical markers will be collected at those same time points. All recipients will have no major medical diagnoses which exclude them from undergoing G-CSF stem cell mobilization and administration of Precise natural Magnetic fields which agree with the recipients own natural magnetic field patterns utilizing an instrument capable of routine clinical therapy use and assessment of response. A physical exam, standard blood chemistry, CBC and hemoglobinopathy testing will be done.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation. Baseline physical exam, blood chemistry will be done on all recipients at baseline. These will be repeated after 3, 6, 9, and 12 months of treatment, and quarterly for 1 year following the completion of treatment.

Example 13

This protocol will assess the efficacy of stem cell activation using the recipients own natural magnetic field patterns to improve the levels of anti-aging bio-markers in the recipients.

Recipients will be treated by administration of Precise natural Magnetic fields to improve the levels of anti-aging biomarkers.

Evaluation of the improvement in the levels of anti-aging biomarkers in the recipients during treatment for one year and for one year following the end of treatments. Recipients who are interested in assessing their level of anti-aging biomarkers, and who are willing to receive stem cell activation using Precise natural Magnetic fields will be treated monthly for a one-year period to determine if there is any improvement in those markers. Recipients will receive precise magnetic field patterns which will agree with their body's own natural magnetic field patterns monthly for 12 months. Assessments measuring the biomarkers will be done prior to the start of treatment and thereafter every 3 months during the treatment period, and every three months for 12 additional months after the completion of the treatment period. Additionally, clinical markers will be collected at those same time points. All recipients will have no major medical diagnoses which exclude them from receiving Precise natural Magnetic fields which agree with the recipients own natural magnetic field patterns utilizing an instrument capable of routine clinical therapy use and assessment of response. A physical exam and standard blood chemistry, CBC will determine their eligibility.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at baseline and at quarterly visits during physical exam that will provide efficacy data for evaluation. Baseline physical exam, blood chemistry and biomarkers markers will be done on all recipients at baseline. These will be repeated after 3, 6, 9, and 12 months of treatment, and quarterly for 1 year following the completion of treatment.

Example 14

This protocol will assess the efficacy of stem cell activation using the recipients own natural magnetic field patterns in combination with infusing autologous stem-cell rich plasma to improve the levels of anti-aging bio-markers in the recipients.

Recipients will be treated with autologous stem cell rich plasma from recipients who have had stem cell mobilization in combination with administration of Precise natural Magnetic fields to improve the levels of anti-aging biomarkers in the recipients. Evaluation of the improvement in the levels of anti-aging biomarkers in the recipients during treatment for one year and for one year following the end of treatment. Recipients who are interested in assessing their level of anti-aging biomarkers, and who are willing to receive doses of autologous stem cell rich donor plasma will be treated monthly for a one-year period to determine if there is any improvement in those markers.

Recipients will receive Autologous Stem Cell Rich plasma in aliquots of 50 ml monthly for 12 months. On the same day they will also receive precise magnetic field patterns which will agree with their body's own natural magnetic field patterns. Assessments measuring the biomarkers will be done every 3 months during the treatment period, and every three months for 12 additional months after the completion of the treatment period. Additionally, clinical markers will be collected at those same time points.

All autologous donors who are also recipients will have no major medical diagnoses which exclude them from undergoing stem cell mobilization. A physical exam and standard blood chemistry, CBC, and Infectious Disease marker testing will determine their eligibility. Their ABO/Rh type will also be tested.

Donors will be dosed with G-CSF at a dose of 5 to 15 ug/kg intravenously or subcutaneously for three days prior to undergoing plasma pheresis. This will stimulate a significantly increased number of stem cells in the plasma. Donors will have Infectious Disease testing repeated on the day of pheresis. ABO/Rh type will also be tested.

The yield of stem cell rich plasma expected from the pheresis is about 2 liters. The plasma will be divided into aliquots of about thirty-six 50 ml doses and 5 ml testing aliquots. Samples will be frozen until such time as the same Plasma Recipient is being treated.

Administration of Precise natural Magnetic fields which agree with the recipients own natural magnetic field patterns utilizing an instrument capable of routine clinical therapy use and response assessment There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation. Baseline physical exam, blood chemistry and infectious disease markers will be done on all plasma donors and recipients at baseline. These apart from infectious disease markers will be repeated after 3, 6, 9, and 12 months of treatment, and quarterly for 1 year following the completion of treatment.

Example 15

This protocol will assess the efficacy of infusing stem-cell rich plasma from ABO-matched healthy donors to improve the levels of anti-aging bio-markers in the recipients. Recipients will be treated with plasma from healthy donors who have had stem cell mobilization to improve the levels of anti-aging biomarkers in the recipients of the plasma.

Recipients who are interested in assessing their level of anti-aging biomarkers, and who are willing to receive doses of donor plasma will be treated monthly for a one-year period to determine if there is any improvement in those markers.

The recipients will receive ABO/Rh cross-matched plasma in aliquots of 50 ml monthly for 12 months. Assessments measuring the biomarkers will be done every 3 months during the treatment period, and every three months for 12 additional months after the completion of the treatment period. Additionally, clinical markers will be collected at those same time points.

All donors will be healthy, young adults (age 30 or less) with no major medical diagnoses. A physical exam and standard blood chemistry and CBC will determine their eligibility. An ABO/Rh typing and antibody panel will be done on each donor, as well as Infectious Disease testing.

Donors will be dosed with G-CSF at a dose of 5 to 15 ug/kg intravenously or subcutaneously for three days prior to undergoing plasma pheresis. This will stimulate a significantly increased number of stem cells in the plasma. Donors will have Infectious Disease testing repeated on the day of pheresis.

The yield of plasma expected from the pheresis is about 2 liters. The plasma will be divided into aliquots of about thirty-six 50 ml doses and 5 ml testing aliquots (for cross matching). Samples will be frozen until such time as a Plasma Recipient of the same ABO/Rh type is being treated. Donors will be restricted to males and nulliparous females to avoid the presence of cytotoxic lymphocyte and granulocyte antibodies.

Recipients can be of any age or gender as long as they have no significant medical issues that would be contraindicated by the infusion of donor plasma. This will be determined by a physical exam and standard blood chemistry and CBC. Their ABO/Rh type will also be tested.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:
1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation. Baseline physical exam, blood chemistry and infectious disease markers will be done on all plasma donors and recipients at baseline. These apart from infectious disease markers will be repeated after 3, 6, 9, and 12 months of treatment, and quarterly for 1 year following the completion of treatment.

Example 16

This protocol will assess the efficacy of infusing stem-cell rich plasma from ABO-matched cord blood donors to improve the levels of anti-aging bio-markers in the recipients.

Recipients will be treated with plasma from Cord Blood donors to improve the levels of anti-aging biomarkers in the recipients of the plasma. Evaluation of the improvement in the levels of anti-aging biomarkers in the recipients during treatment for one year and for one year following the end of treatment. Improvement of clinical markers of aging as reported via a 13-item Clinical evaluation.

Recipients who are interested in assessing their level of anti-aging biomarkers, and who are willing to receive doses of donor plasma monthly for a one-year period will be treated to determine if there is any improvement in those markers.

The recipients will receive ABO/Rh cross-matched Cord Blood Plasma in aliquots of 50 ml monthly for 12 months. Assessments measuring the biomarkers will be done every 3 months during the treatment period, and every three months for 12 additional months after the completion of the treatment period. Additionally, clinical markers will be collected at those same time points.

All donations of cord blood plasma will be taken from the plasma extracted and normally discarded from healthy babies cord blood collected from the delivered placenta at the time of birth and whose stem cells are to be cryopreserved for the baby's personal use at a later date. The baby and mother will have no major medical diagnoses and the mother will sign an informed consent form and agree to donate plasma. A physical exam and standard blood chemistry and CBC will determine their eligibility. An ABO/Rh typing and antibody panel will be done on each donor, as well as Infectious Disease testing. The yield of plasma expected from the cord blood is about 55 mls. The plasma will be divided into aliquots of about 50 ml doses and 5 ml testing aliquots (for cross matching). Samples will be frozen until such time as a Plasma Recipient of the same ABO/Rh type is being treated.

Recipients can be of any age or gender as long as they have no significant medical issues that would be contraindicated by the infusion of donor plasma. This will be determined by a physical exam and standard blood chemistry and CBC. Their ABO/Rh type will also be tested.

There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

Example 18

This protocol will assess the efficacy of G-CSF (granulocyte colony stimulating factor) mobilization of CD34+ peripheral blood stem cells to improve the levels of anti-aging bio-markers in the recipients.

Patients will be treated with stem cell mobilization factor to improve the levels of anti-aging biomarkers in the recipients. Evaluation of the improvement in the levels of anti-aging biomarkers in the recipients during treatment for one year and for one year following the end of treatment. Improvement of clinical markers of aging as reported via a 13-item Clinical evaluation.

Recipients who are interested in assessing their level of anti-aging biomarkers, and who are willing to receive G-CSF Mobilization for a one-year period will be treated to determine if there is any improvement in those markers.

The recipients will receive initially 3 cycles of G-CSF mobilization followed by 1 cycle at 3 months, 6 months, 9 months and 12 months. Each Cycle consists of daily G-CSF at a dose of 5 to 15 ug/kg intravenously or subcutaneously per day administered subcutaneously for 3 to 7 days followed by 7 days off G-CSF with evaluation on 3 of the 7 off days. Assessments measuring the biomarkers will be done every 3 months during the treatment period, and every three months for 12 additional months after the completion of the treatment period. Additionally, clinical markers will be collected at those same time points.

Recipients who sign an informed consent form can be of any age or gender as long as they have no significant medical issues that would be contraindicated by the subcutaneous administration of G-CSF. This will be determined by a physical exam and standard blood chemistry and CBC. Their hemoglobinopathy screen will also be tested. There will be eight primary biomarker measurements evaluated at baseline, and after treatment for 3 months, 6 months, 9 months, and 12 months. These same evaluations will continue every three months for an additional year to examine the long-term effect of the treatment. These assessments are:

1. Immunosenescence Panel
2. CCL 11
3. TGFBeta 1 growth factor
4. Nuclear Factor kappa beta (NFkB)
5. DHEA-S
6. Plasma Insulin
7. Telomere length
8. Cytokine Multiplex 18

There will also be clinical markers (group of 13) evaluated at the quarterly visits during physical exam that will provide secondary efficacy data for evaluation.

In accordance with the protocol set forth in Example 18, several patients were treated. These patients, their conditions, and treatment will now be summarized with reference to FIGS. 13-29.

Figure 13:
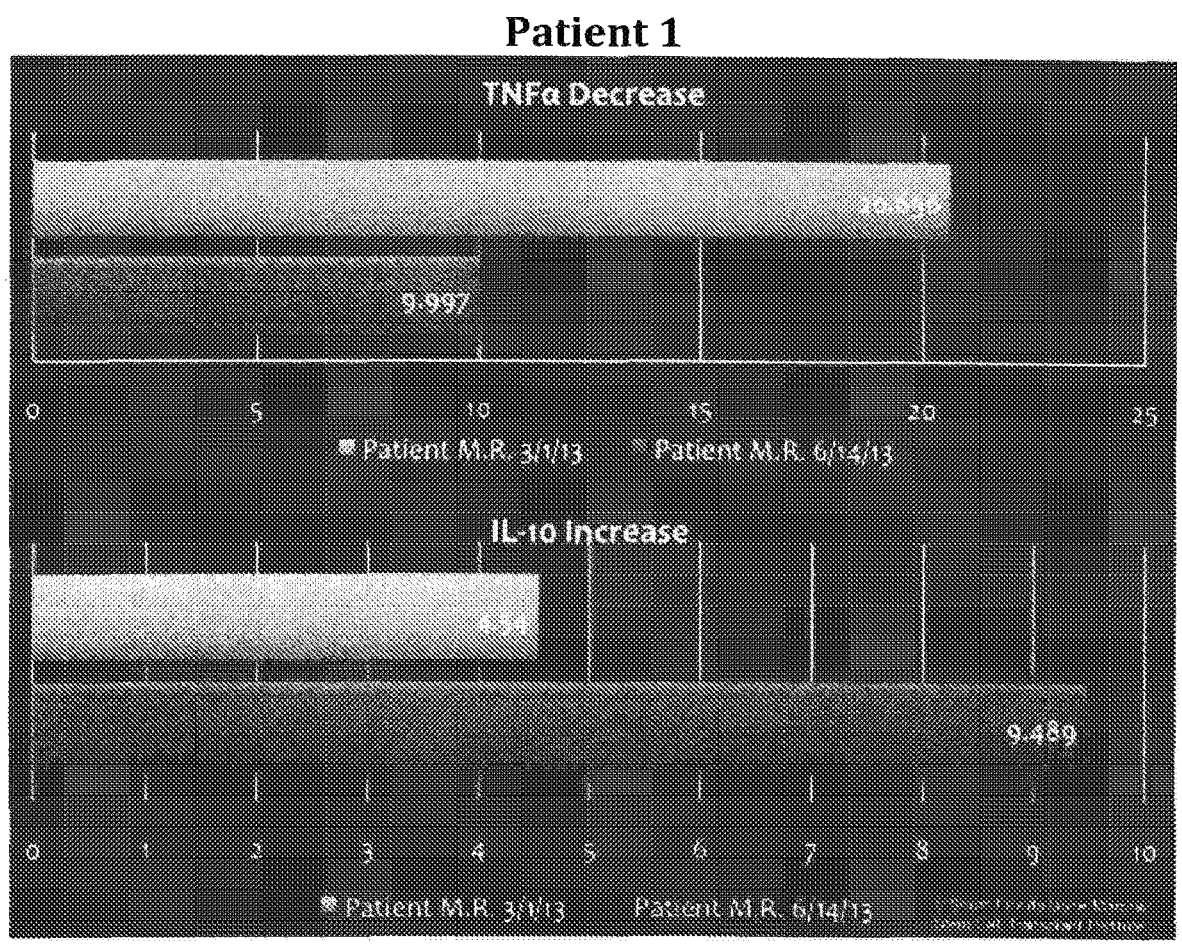
FIG. 13 illustrates an effect of the inventive method on regulation of levels of inflammatory and non-inflammatory markers in Patient 1.

Regarding Patient 1, reference is made to FIG. 13.

Diagnosis: Anemia, Chronic Disease (Chronic Obstructive Pulmonary Disease), Cardiovascular Disease (Chronic Heart Failure), Protein energy malnutrition, and Frailty.

In accordance with the basic protocol outlined in Example 18, a patient MR was treated with stem cell mobilization factor, G-CSF to improve the levels of anti-aging biomarkers in the patient. Evaluation of the levels of anti-inflammatory (IL-10) and inflammatory (TNF-alpha) aging biomarkers during treatment was carried out. An improvement in the level of the clinical marker of aging, IL-10 was reported. After 3 months of treatment, during which time the patient was administered G-CSF as in Example 18, levels of IL-10 improved from 4.54 to 9.489.

Evaluation of the improvement in the levels of inflammatory aging biomarkers during treatment was carried out. A decrease in the level of the inflammatory clinical marker of aging, TNF-alpha was reported. After 3 months of treatment, during which time the patient was administered G-CSF as in Example 18, levels of TNF-alpha went from 20.636 to 9.997.

While not wishing to be bound to any particular theory of operation, reduction in TNF-alpha and increase in IL-10 resulted in improvement in clinical symptoms of inflammation and immunosenescence associated with Anemia, Chronic Disease (Chronic Obstructive Pulmonary Disease,), Cardiovascular Disease (Chronic Heart Failure), Protein energy malnutrition, Frailty.

Figure 14:
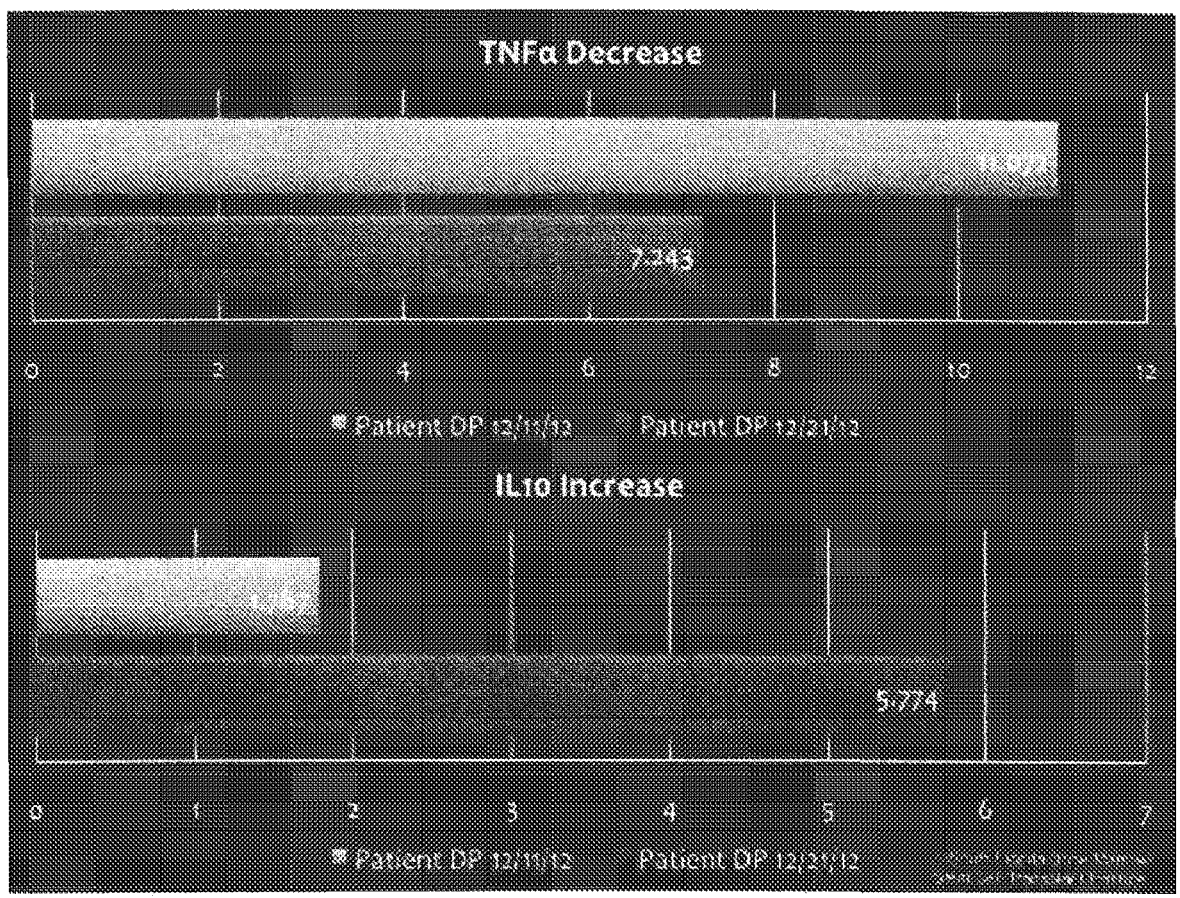
FIG. 14 illustrates an effect of the inventive method on regulation of levels of inflammatory and non-inflammatory markers in Patient 2.
Figure 15:
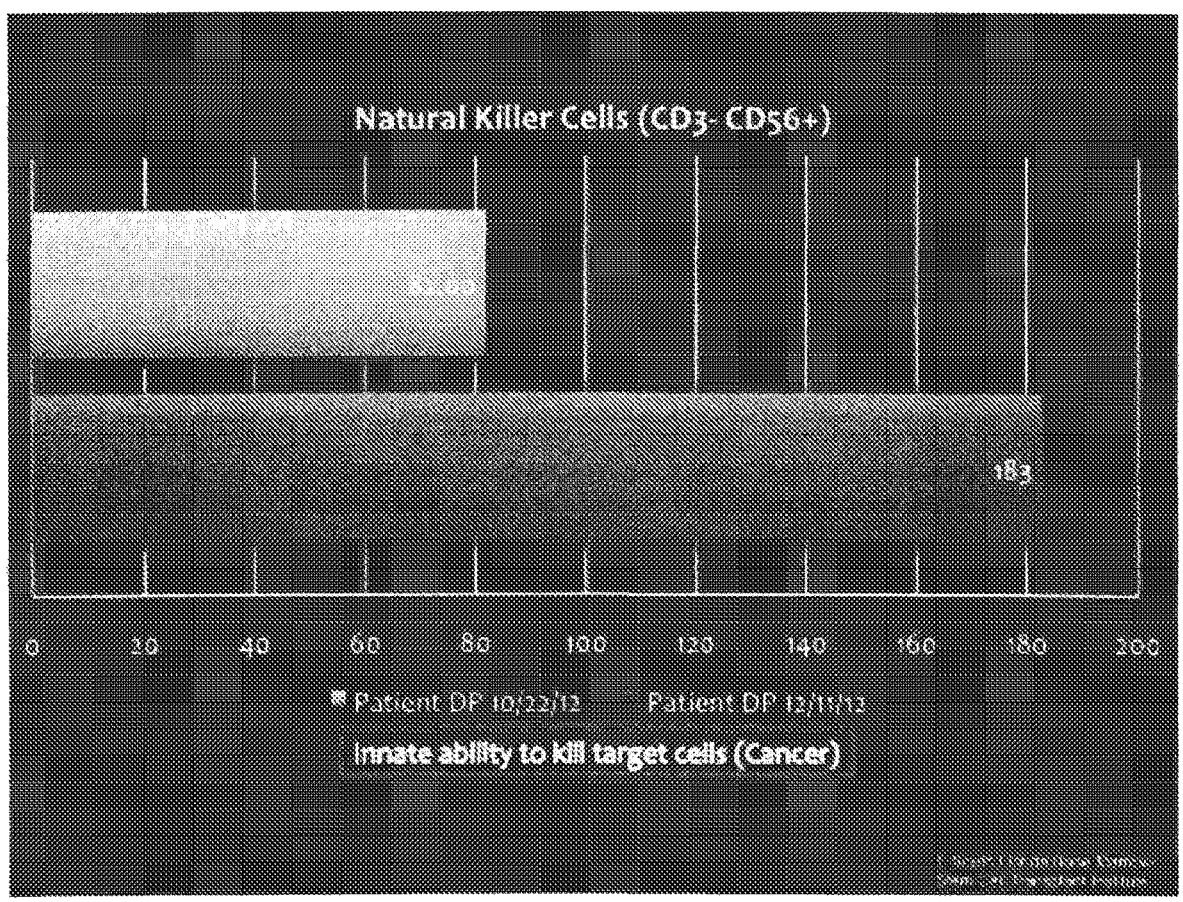
FIG. 15 illustrates an effect of the inventive method on regulation of levels of natural killer cells in Patient 2.

Regarding Patient 2, reference is made to FIGS. 14 and 15.

Diagnosis: Cancer, Protein energy malnutrition, Frailty.

In accordance with the basic protocol outlined in Example 18, a patient DP was treated with stem cell mobilization factor, G-CSF to improve the levels of aging biomarkers in the patient. Evaluation of the levels of anti-inflammatory (IL-10) and inflammatory (TNF-alpha) aging biomarkers during treatment was carried out. An improvement in the level of the clinical marker of aging, IL-10 was reported.

After 3 months of treatment, during which time the patient was administered G-CSF as in Example 18, levels of IL-10 improved from 1.787 to 5.774.

Evaluation of the improvement in the levels of inflammatory aging biomarkers during treatment was carried out. A decrease in the level of the inflammatory clinical marker of aging, TNF-alpha was reported. After 3 months of treatment, during which time the patient was administered G-CSF as in Example 18, levels of TNF-alpha decreased from 11.072 to 7.243. After 3 months of treatment, during which time the patient was administered G-CSF as in Example 18, levels of Natural Killer Cells increased from 82 to 183.

While not wishing to be bound to any particular theory of operation, reduction in TNF-alpha and increase in IL-10 and Natural Killer Cells resulted in improvement in clinical symptoms of inflammation and immunosenescence associated with Cancer, Protein energy malnutrition, Frailty.

Figure 16:
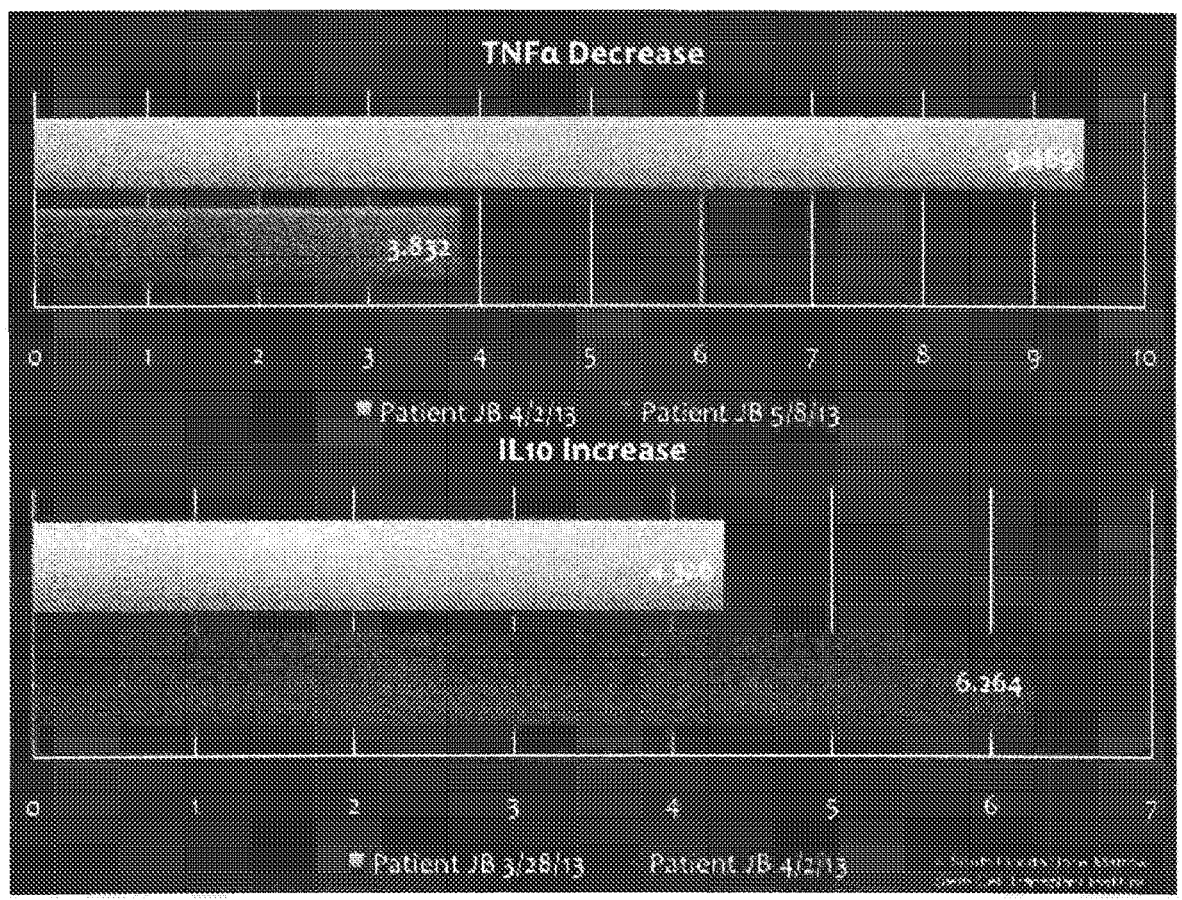
FIG. 16 illustrates an effect of the inventive method on regulation of levels of inflammatory and non-inflammatory markers in Patient 3.

Regarding Patient 3, reference is made to FIG. 16.

Diagnosis: Chronic disease, Neurodegenerative Disease, Frailty.

In accordance with the basic protocol outlined in Example 18, a patient JB was treated with stem cell mobilization factor, G-CSF to improve the levels of aging biomarkers in the patient. Evaluation of the levels of anti-inflammatory (IL-10) and inflammatory (TNF-alpha) aging biomarkers during treatment was carried out. An improvement in the level of the clinical marker of aging, IL-10 was reported. After 3 months of treatment, during which time the patient was administered G-CSF as in Example 18, levels of IL-10 improved from 4.326 to 6.264.

Evaluation of the improvement in the levels of inflammatory aging biomarkers during treatment was carried out. A decrease in the level of the inflammatory clinical marker of aging, TNF-alpha was reported. After 3 months of treatment, during which time the patient was administered G-CSF as in Example 18, levels of TNF-alpha decreased from 9.469 to 3.832.

While not wishing to be bound to any particular theory of operation, reduction in TNF-alpha and increase in 1 L-10 resulted in improvement in clinical symptoms of inflammation and immunosenescence associated with Chronic disease, Neurodegenerative Disease, Frailty.

Figure 17:
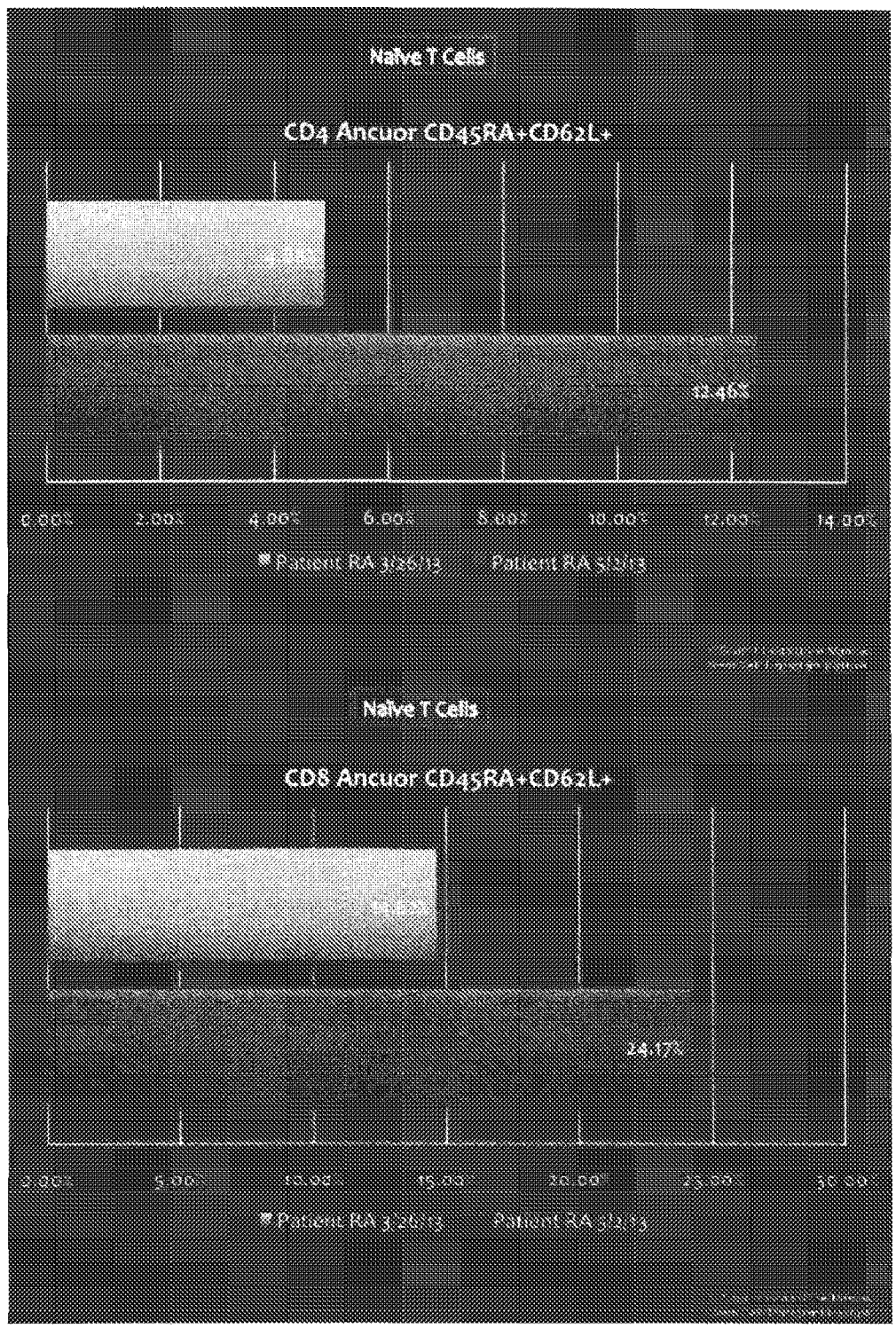
FIG. 17 illustrates an effect of the inventive method on regulation of levels of naïve T cells in Patient 4.
Figure 18:
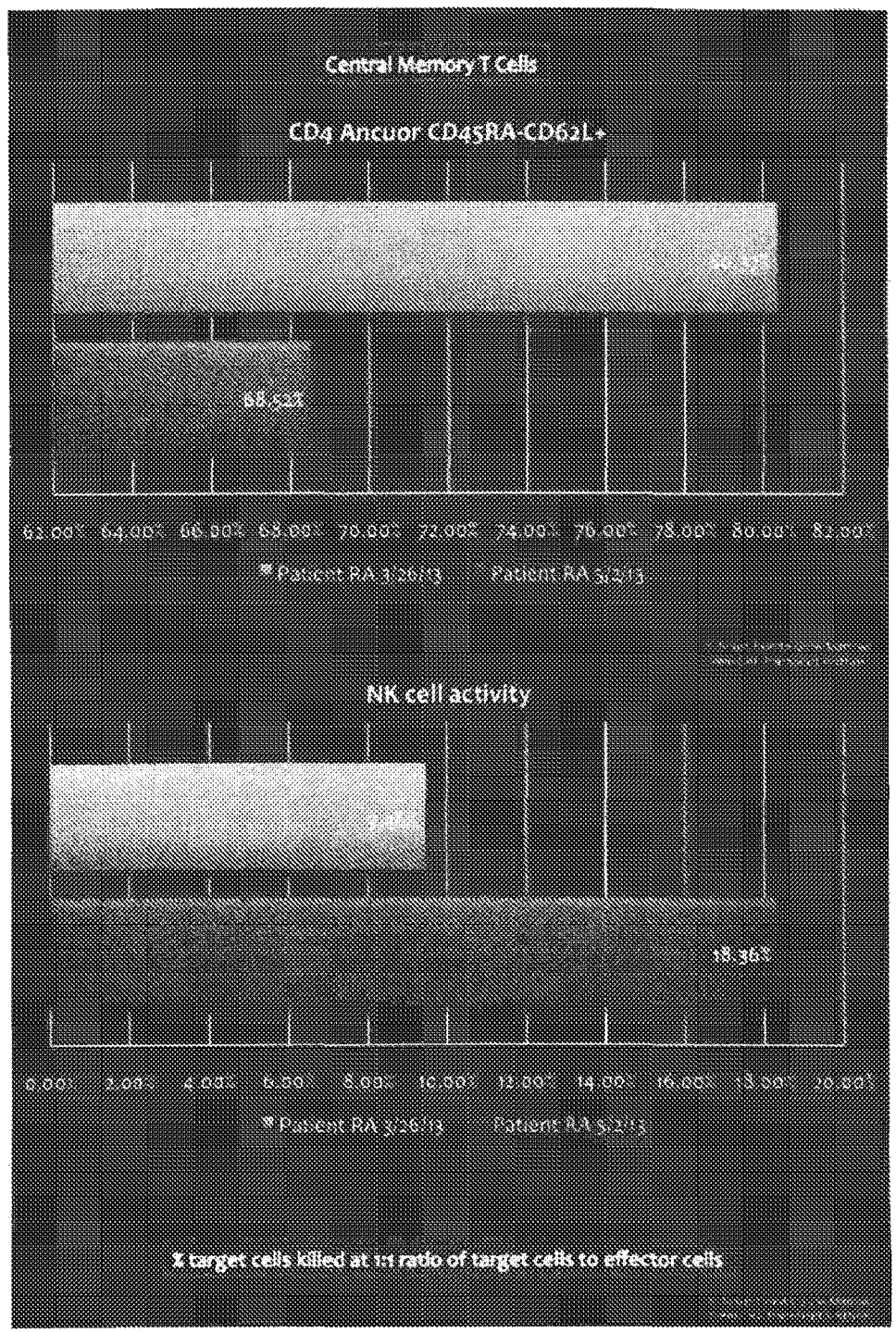
FIG. 18 illustrates an effect of the inventive method on regulation of levels of Central Memory T cells and Natural Killer cell activity in Patient 4.

Regarding Patient 4, reference is made to FIGS. 17 and 18.

Diagnosis: Chronic Metabolic Disease, Diabetes Mellitus Type 2, Frailty.

In accordance with the basic protocol outlined in Example 18, a patient RA was treated with stem cell mobilization factor, G-CSF to improve the levels of aging biomarkers in the patient. Evaluation of the improvement in the levels of aging, immunosenescence, immune dysfunction, and early lymphoid lineage differentiation biomarkers during treatment was carried out. An improvement with an increase in the level of the Naïve CD4 and CD8 levels and a decrease in the Memory CD4 T cells and improvement in Natural Killer Cell Activity were reported. After 2 months of treatment, during which time the patient was administered G-CSF as in Example 18, levels of Naïve CD4 improved from 4.88 to 12.46. Levels of Naïve CD8 improved from 14.62 to 24.17.

Evaluation of the improvement was observed with a decrease in the levels of Memory CD4 T Cells from 80.37 to 68.52.

Also an improvement in Natural Killer Cell Activity was reported After 2 months of treatment, during which time the patient was administered G-CSF as in Example 18, wherein levels of Natural Killer Cell Activity CD4 improved from 9.46 to 18.36.

While not wishing to be bound to any particular theory of operation, reduction in Central Memory T cells and increase in Naïve T cells and Natural Killer Cell Activity resulted in improvement in clinical symptoms of immune dysfunction, immunosenescence and impairment of early lymphoid differentiation associated with Chronic Metabolic Disease, Diabetes Mellitus Type 2, and Frailty.

Figure 19:
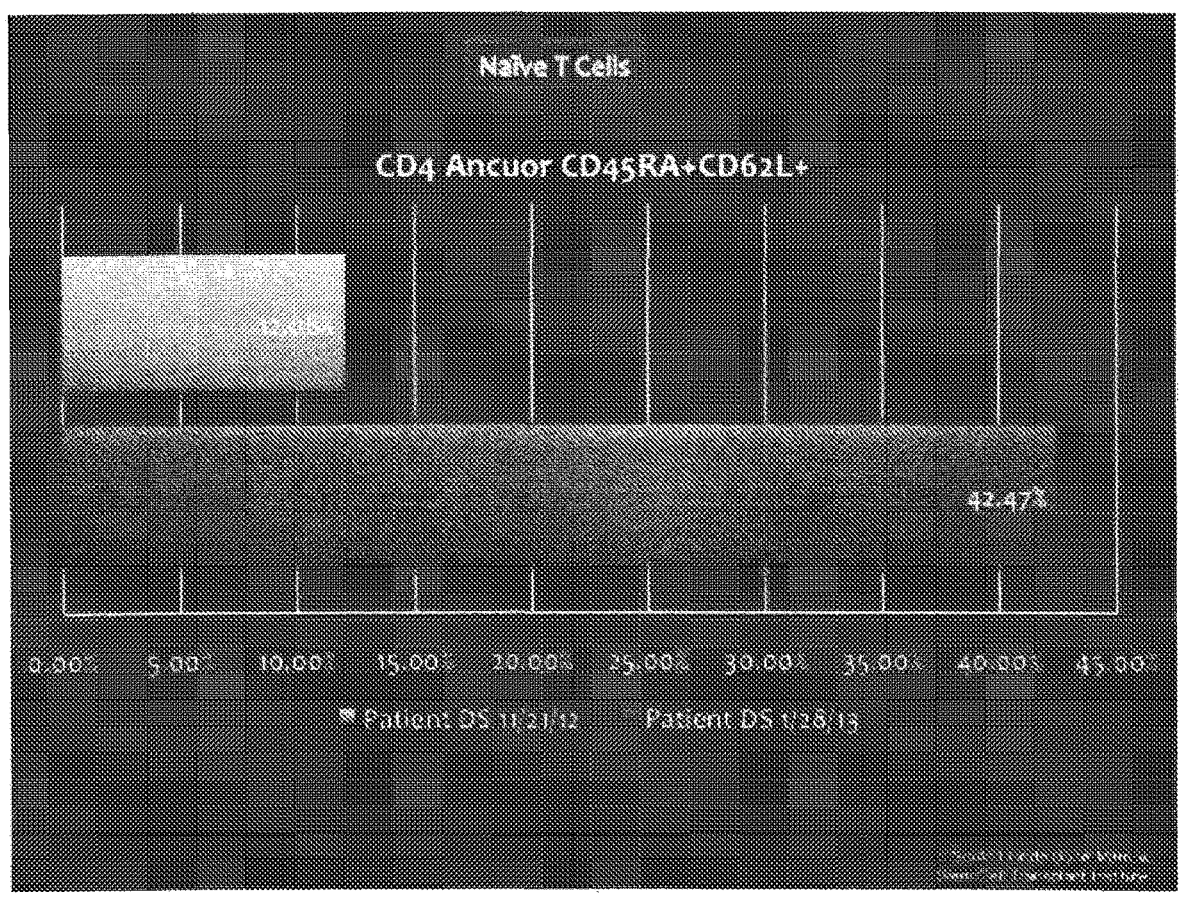
FIG. 19 illustrates an effect of the inventive method on regulation of levels of naïve T cells in Patient 5.
Figure 20:
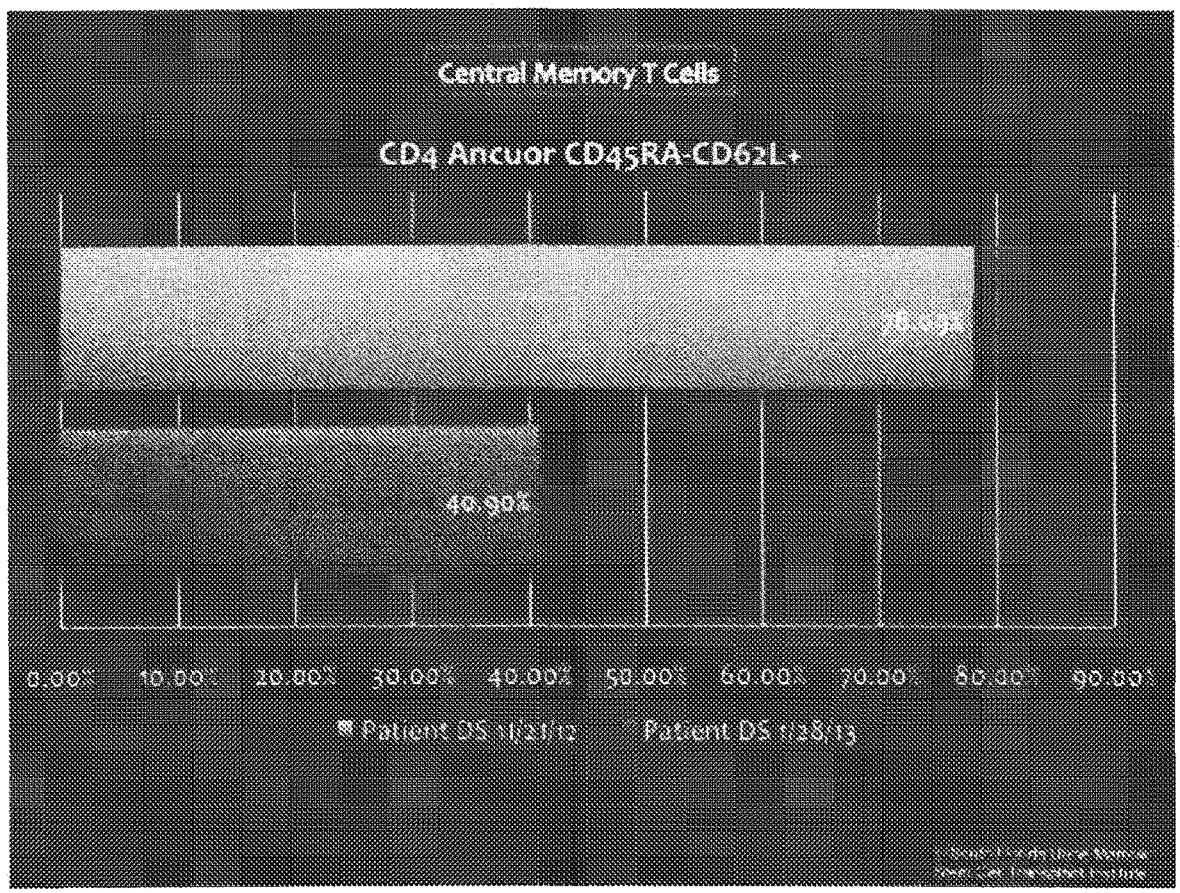
FIG. 20 illustrates an effect of the inventive method on regulation of levels of Central Memory T cells in Patient 5.
Figure 21:
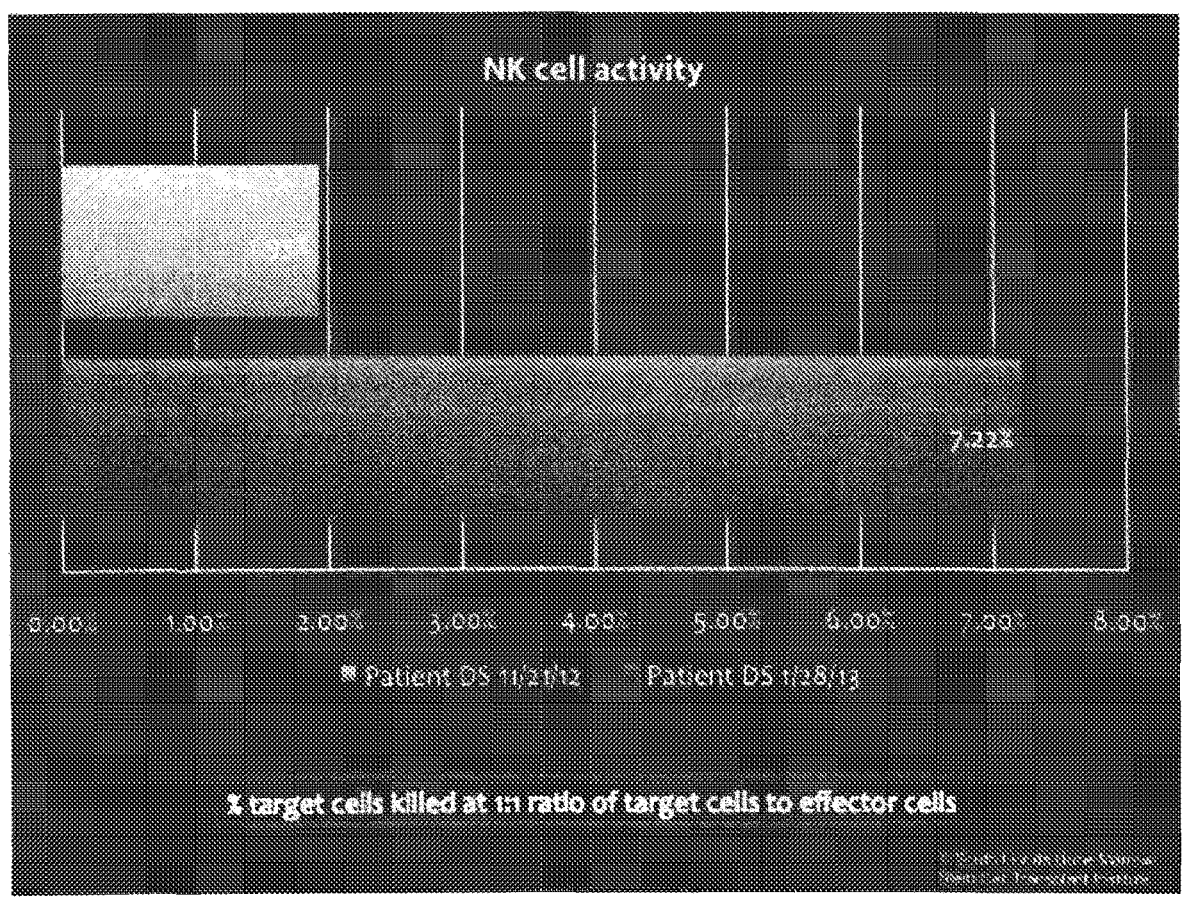
FIG. 21 illustrates an effect of the inventive method on regulation of levels of Natural Killer cell activity in Patient 5.

Regarding Patient 5, reference is made to FIGS. 19-21.

Diagnosis: Chronic disease, Cancer (Waldenstroms Macroglobulinemia), Neurodegenerative Disease (Peripheral Neuropathy), Frailty.

In accordance with the basic protocol outlined in Example 18, a patient DS was treated with stem cell mobilization factor, G-CSF to improve the levels of aging biomarkers in the patient. Evaluation of the improvement in the levels of aging, immunosenescence, immune dysfunction, and early lymphoid lineage differentiation biomarkers during treatment was carried out. An improvement with an increase in the level of the Naïve CD4 levels and a decrease in the Memory CD4 T cells and improvement in Natural Killer Cell Activity was reported. After 2 months of treatment, during which time the patient was administered G-CSF as in Example 18, levels of Naïve CD4 improved from 12.08 to 42.47.

Evaluation of the improvement in immune dysfunction was further observed with a decrease in the levels of Memory CD4 T Cells decreased from 78.09 to 40.90.

Also an improvement in Natural Killer Cell Activity was reported. After 2 months of treatment, during which time the patient was administered G-CSF as in Example 18, levels of Natural Killer Cell Activity CD4 improved from 1.93 to 7.22.

While not wishing to be bound to any particular theory of operation, reduction in Central Memory T cells and increase in Naïve T cells and Natural Killer Cell Activity resulted in improvement in clinical symptoms of immune dysfunction, immunosenescence and impairment of early lymphoid differentiation associated with Chronic disease, Cancer (Waldenstroms Macroglobulinemia), Neurodegenerative Disease (Peripheral Neuropathy), and Frailty.

Figure 22:
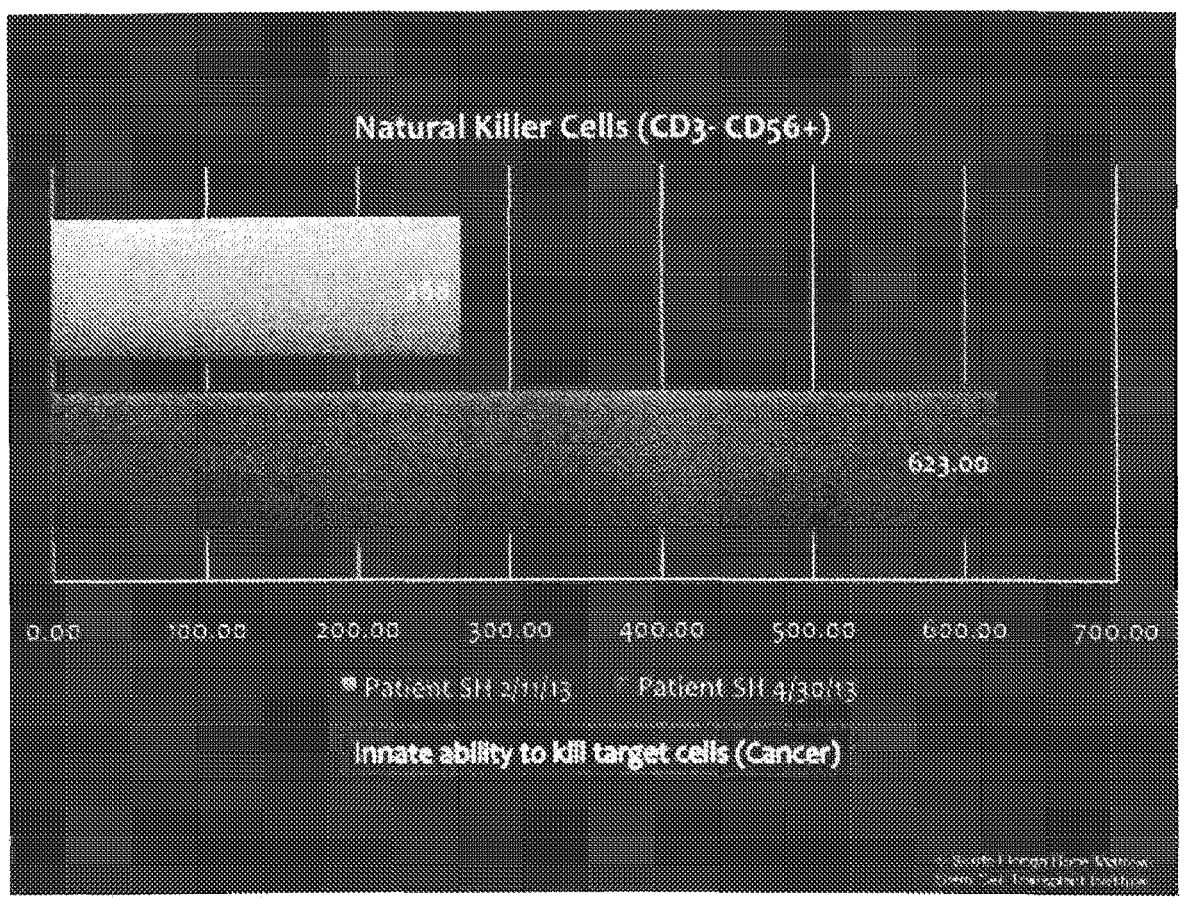
FIG. 22 illustrates an effect of the inventive method on regulation of levels of Natural Killer cell activity in Patient 6.

Regarding Patient 6, reference is made to FIG. 22.

Diagnosis: Chronic disease, Chronic Infection (Lyme's Disease), Neurodegenerative Disease.

In accordance with the basic protocol outlined in Example 18, a patient SH was treated with stem cell mobilization factor, G-CSF to improve the levels of aging biomarkers in the patient. Evaluation of the improvement in the levels of aging, immunosenescence, and immune dysfunction biomarkers during treatment was carried out. An improvement with an increase in the level of Natural Killer Cells was reported. After 2 months of treatment, during which time the patient was administered G-CSF as in Example 18, levels of Natural Killer Cells improved from 268 to 623.

While not wishing to be bound to any particular theory of operation increase in Natural Killer Cells resulted in improvement in clinical symptoms of immune dysfunction, and immunosenescence associated with Chronic disease, Chronic Infection (Lyme's Disease), and Neurodegenerative Disease.

Figure 23:
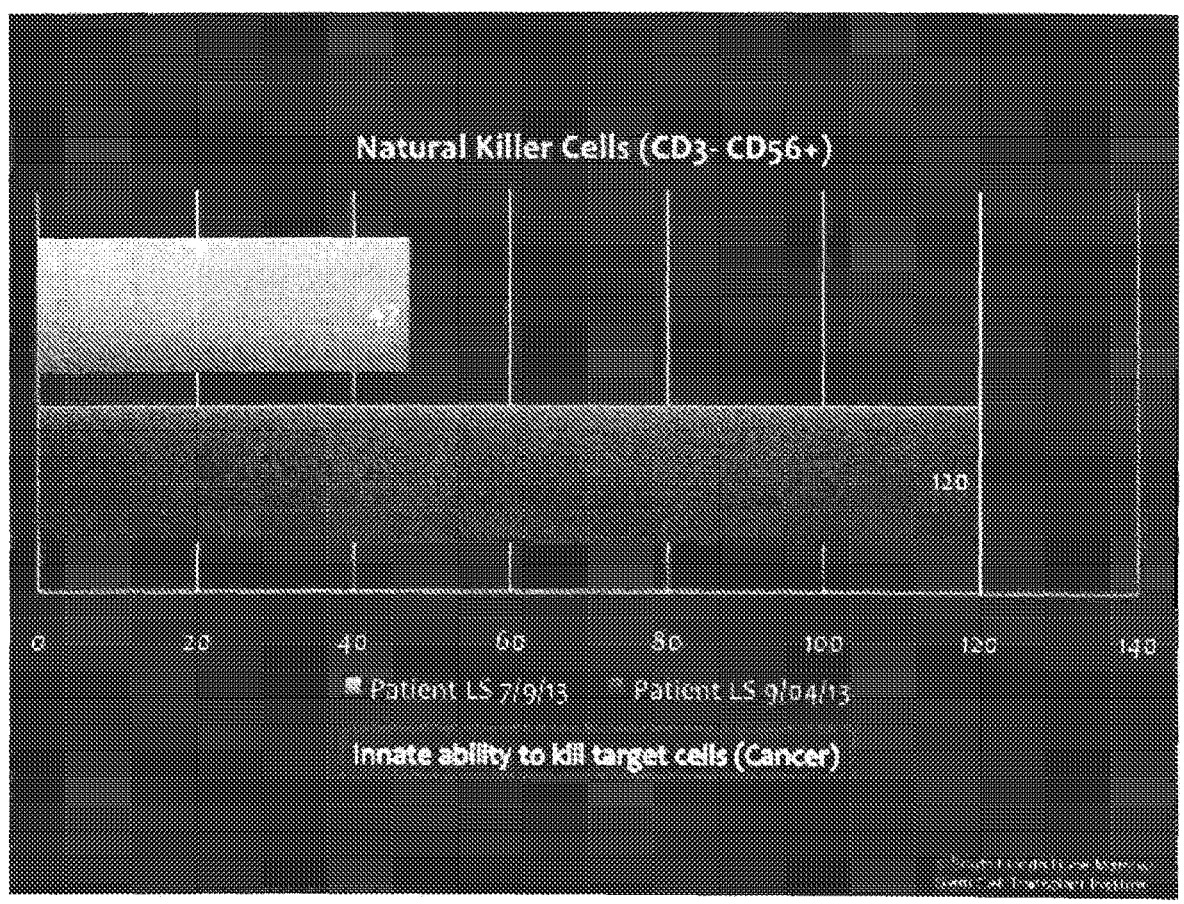
FIG. 23 illustrates an effect of the inventive method on regulation of levels of Natural Killer cell activity in Patient 7.
Figure 24:
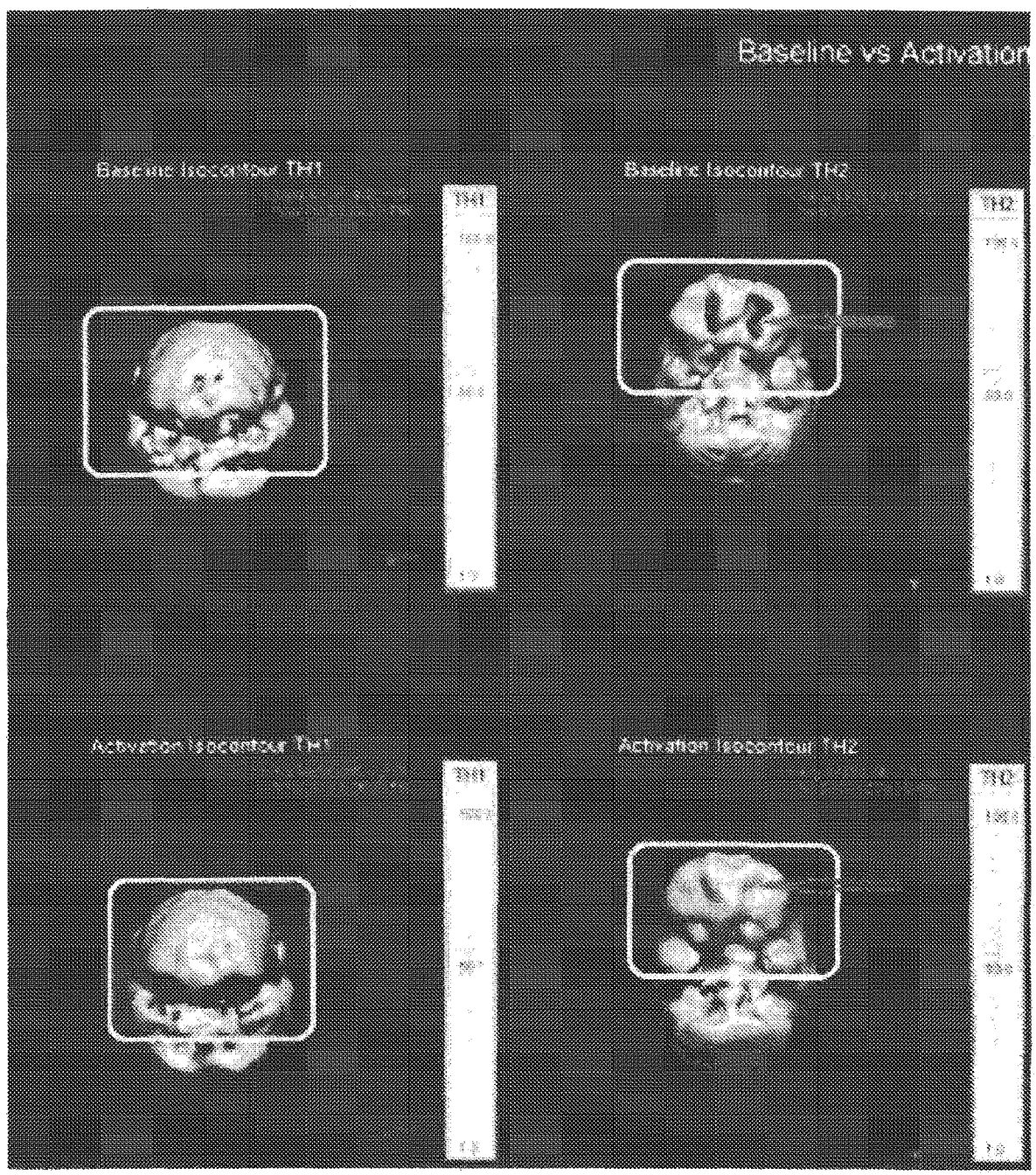
FIG. 24 is a SPECT Scan which demonstrates improvement in the patients Neurodegenerative Disease following treatment in accordance with the invention.

Regarding Patient 7, reference is made to FIGS. 23 and 24.

Diagnosis: Chronic disease, Chronic Fatigue Syndrome, Neurodegenerative Disease, Autoimmune Disease (Type 1 Diabetes Mellitus).

In accordance with the basic protocol outlined in Example 18, a patient LS was treated with stem cell mobilization factor, G-CSF to improve the levels of aging biomarkers in the patient. Evaluation of the improvement in the levels of aging, immunosenescence, and immune dysfunction biomarkers during treatment was carried out. An improvement with an increase in the level of Natural Killer Cells was reported. After 2 months of treatment, during which time the patient was administered G-CSF as in Example 18, levels of Natural Killer Cells improved from 47 to 120.

After the 2 months of treatment, during which time the patient was administered G-CSF as in Example 18 SPECT Scans (FIG. 24) showed improvement in the patients Neurodegenerative Disease.

After the 2 months of treatment, during which time the patient was administered G-CSF as in Example 18 the patient's insulin requirement for Type 1 Diabetes Mellitus decreased by 50%.

While not wishing to be bound to any particular theory of operation, increase in Natural Killer Cells and results of SPECT Scans were indicative of improvement in clinical symptoms of immune dysfunction and immunosenescence associated with Chronic disease, Chronic Fatigue Syndrome, Neurodegenerative Disease and Type 1 Diabetes Mellitus.

Figure 25:
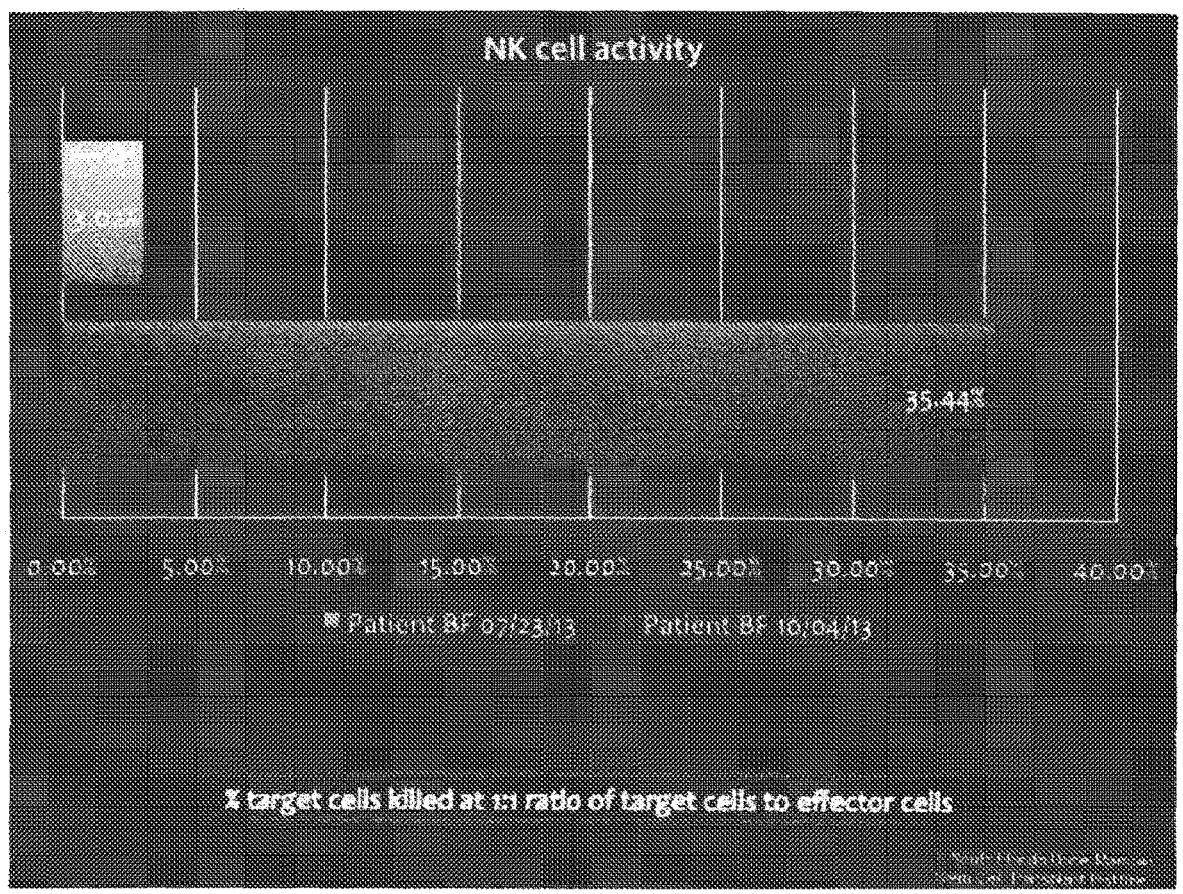
FIG. 25 illustrates an effect of the inventive method on regulation of levels of Natural Killer cell activity in Patient 8.
Figure 26:
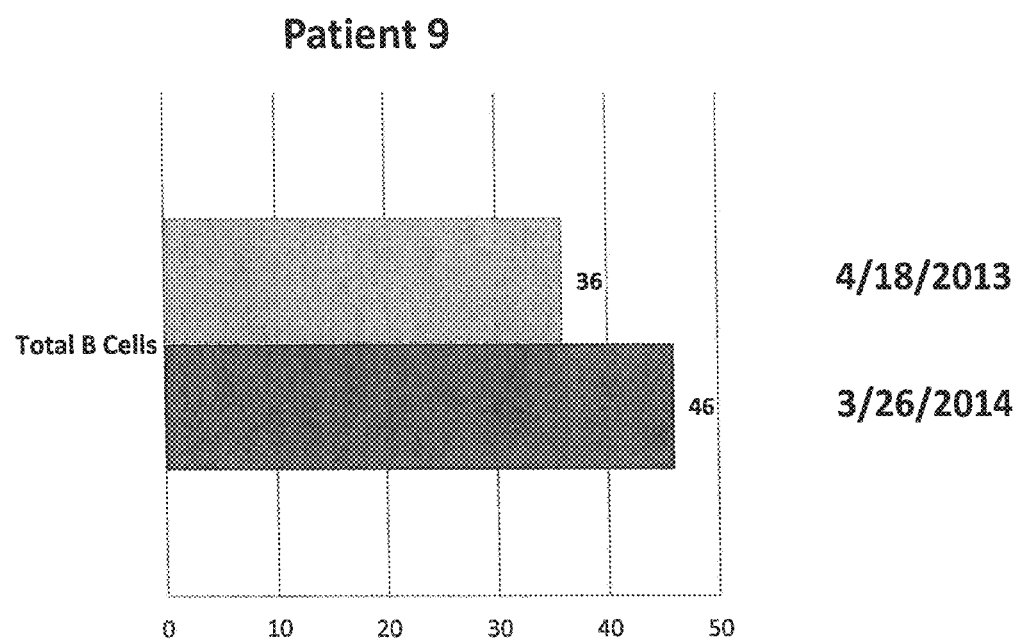
FIG. 26 illustrates an effect of the inventive method on regulation of levels of Total B cells in Patient 9.
Figure 27:
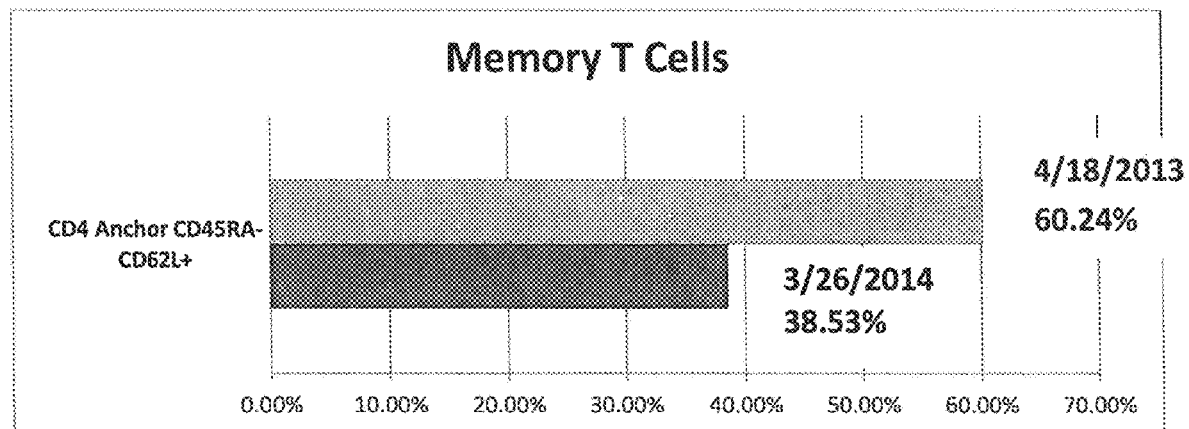
FIG. 27 illustrates an effect of the inventive method on regulation of levels of Memory T cells in Patient 9.
Figure 28:
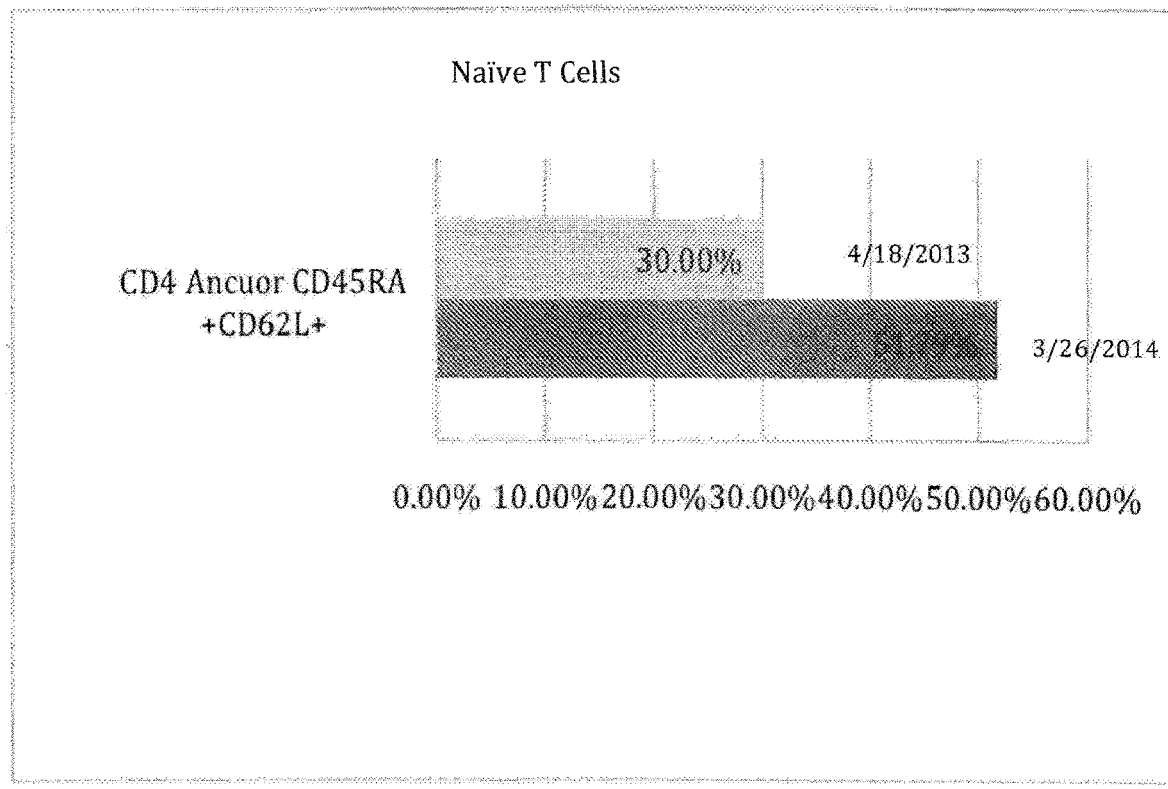
FIG. 28 illustrates an effect of the inventive method on regulation of levels of naïve T cells in Patient 9.
Figure 29:
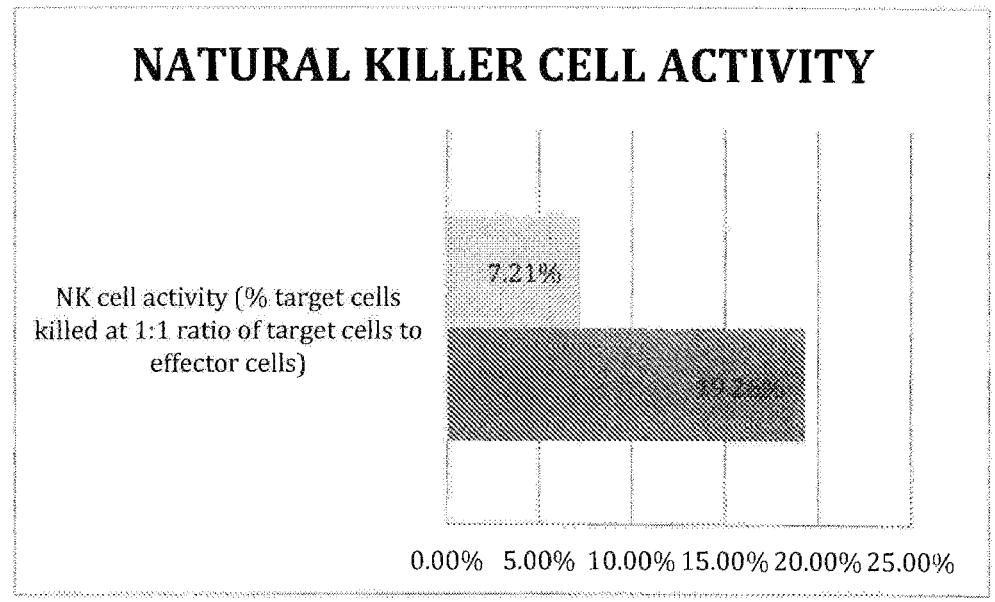
FIG. 29 illustrates an effect of the inventive method on regulation of levels of Natural Killer cell activity in Patient 9.

Regarding Patient 8, reference is made to FIG. 25.

Diagnosis: Chronic disease, Chronic Viral Infection

In accordance with the basic protocol outlined in Example 18, a patient BF was treated with stem cell mobilization factor, G-CSF to improve the levels of aging biomarkers in the patient. Evaluation of the improvement in the levels of aging, immunosenescence, and immune dysfunction biomarkers during treatment was carried out. An improvement with an increase in the level of Natural Killer Cells Activity was reported. After 2 months of treatment, during which time the patient was administered G-CSF as in Example 18, levels of Natural Killer Cells Activity improved from 3.02 to 35.44.

While not wishing to be bound to any particular theory of operation, increase in Natural Killer Cells resulted in improvement in clinical symptoms of immune dysfunction and immunosenescence associated with Chronic disease and Chronic Viral Infection.

Regarding Patient 9, reference is made to FIGS. 26-29.

Diagnosis: Chronic disease, Cancer (Colon Cancer), Frailty.

In accordance with the basic protocol outlined in Example 5, a patient LK was treated with stem cell activation with stem cell mobilization with granulocyte colony stimulating factor (G-CSF) and in combination with infusing stem-cell rich plasma from ABO-matched healthy allogeneic donors to improve the levels of anti-aging biomarkers in the recipients.

Evaluation of the improvement in the levels of aging, immunosenescence, immune dysfunction, and early lymphoid lineage differentiation biomarkers during treatment was carried out. An improvement with an increase in the level of the Naïve CD4 levels and a decrease in the Memory CD4 T cells and improvement in Natural Killer Cell Activity was reported. After 12 months, during which time the patient was administered G-CSF as in Example 5, levels of Naïve CD4 cells improved from 30.00 to 51.79

Evaluation of the improvement in immune dysfunction resulted in a decrease in the levels of Memory CD4 T Cells from 60.24 to 38.53.

Also an improvement in Natural Killer Cell Activity was reported After 12 months, during which time the patient was treated as in Example 5, wherein levels of Natural Killer Cell Activity improved from 7.21 to 19.26.

Also an improvement in B Cell was reported. After 12 months of treatment, during which time the patient was treated as in Example 5, wherein levels of B Cells improved from 36 to 46.

While not wishing to be bound to any particular theory of operation, reduction in Central Memory T cells and increase in Naïve T cells, B Cells and Natural Killer Cell Activity resulted in improvement in clinical symptoms of immune dysfunction, immunosenescence and impairment of early lymphoid differentiation associated with Chronic disease, Cancer (Colon Cancer), Frailty.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of preparing an allogeneic stem cell rich plasma composition for use in an aging subject comprising:
   a) administering to a young healthy donor a stem cell mobilization agent in an amount and for a time period sufficient to stimulate a significantly increased number of stem cells in the blood of said donor, wherein the stem cell mobilization agent is granulocyte colony stimulating factor (G-CSF);
   b) obtaining a sufficient volume of plasma by plasmapheresis from said donor blood by separating cellular material from the blood and retaining the stem cell rich plasma;
   c) determining the ABO/Rh blood type of said donor; and
   d) optionally storing the plasma collected from said donor until an ABO/Rh blood type matched aging recipient is identified for receipt of said plasma or aliquots of said plasma such that when infused into said recipient in a sufficient amount and for a sufficient time, the plasma composition induces a change in at least one or a combination of biomarkers, thereby preparing the allogenic stem cell rich plasma composition.

2. The method of claim 1, wherein the at least one or a combination of biomarkers is selected from the group consisting of:

the level of nave CD4 cells increases;
(ii) the level of memory CD4 cells decreases;
(iii) the level of nave CD8 cells increases;
(iv) the level of natural killer cells increases;
(v) the level of IL-10 increases;
(vi) the level of TNF alpha decreases; and
(vii) the level of B cells increases.

3. The method of claim 1, wherein said donor is a healthy young adult donor administered G-CSF in an amount and for a time period sufficient to stimulate a significantly increased number of stem cells in the blood of said donor prior to obtaining a sufficient volume of blood from said donor to produce said volume of said plasma from said blood of said donor.

4. The method of claim 3, wherein G-CSF is administered to said donor for about three days prior to obtaining said plasma.

5. The method of claim 3, wherein biomarkers affected by administration of said composition to said recipient are selected from Immunosenescence markers, CCL 11, TGF-Beta 1 growth factor, Nuclear Factor kappa beta (NFkB), Dehydroepiandrosterone sulfate (DHEA-S), Plasma Insulin, Telomere length, cytokines, tumor necrosis factor-alpha (TNF-alpha), Interleukin-10 (IL-10), natural killer cells, naïve T cells, Memory T cells, total B cells, and combinations thereof.

6. The method of claim 3, wherein said G-CSF is administered to said donor at a dose of from about 5 to about 15 µg/kg.

7. The method of claim 3, wherein said plasma is stored as frozen aliquots until such time as a recipient of the same ABO/Rh type as the donor is available to receive said plasma.

8. The method of claim 7, wherein said aliquots are sufficient for administering to a recipient on a monthly basis.

9. The method of claim 8, wherein said aliquots are sufficient for 12 months of recipient treatment.

10. The method of claim 8, wherein the plasma is formulated for intravenous administration.

11. The method of claim 7, wherein said aliquots of said donor plasma are 50 ml aliquots.

12. The method of claim 1, further comprising an additional administering step selected from the group consisting of:

administering to said recipient doses of G-CSF;
(ii) administering to said recipient doses of stem cell enriched allogeneic plasma extracted from normally discarded cord blood collected from the delivered placenta at the time of birth of healthy babies matched to the ABO/Rh blood type of said recipient;
(iii) administering to said recipient precise magnetic field patterns which agree with said recipient's own natural magnetic field patterns; and
(iv) combinations of (i-iii).

13. The method according to claim 12, wherein the recipient experiences:

a) an increase in IL-10 and a reduction in TNF-alpha in a recipient suffering from anemia, chronic disease, cardiovascular disease, protein energy malnutrition, and frailty;
b) an increase in IL-10, a decrease in TNF-alpha, and an increase in natural killer cells in a recipient suffering from cancer, protein energy malnutrition, frailty;
c) an increase in IL-10, a decrease in TNF-alpha, and an increase in natural killer cells in a recipient suffering from chronic disease, neurodegenerative disease, frailty;
d) an increase in naïve CD4 and naïve CD8 cells, and a reduction in memory CD4 cells in a recipient suffering from chronic metabolic disease, diabetes mellitus type 2, frailty;
e) an increase in naïve CD4 and a reduction in memory CD4 cells, and an increase in natural killer cells in a recipient suffering from chronic disease, cancer, neurodegenerative disease, frailty;
f) an increase in natural killer cells in a recipient suffering from chronic disease, chronic infection, neurodegenerative disease;
g) an increase in natural killer cells, improvement in neurodegenerative disease, and reduction in the need for insulin in a recipient suffering from chronic disease, chronic fatigue syndrome, neurodegenerative disease, autoimmune disease;
h) an increase in natural killer cells in a recipient suffering from chronic disease, chronic viral infection; and/or
i) an increase in naïve CD4 cells, a decrease in memory CD4 cells, an increase in killer cells, and an increase in B cells in a recipient suffering from chronic disease, cancer, frailty.

* * * * *